United States Patent
Hallberg

(10) Patent No.: US 9,750,457 B2
(45) Date of Patent: Sep. 5, 2017

(54) SYSTEM AND METHOD FOR DETERMINING POOR SENSOR CONTACT IN A MULTI-SENSOR DEVICE

(71) Applicant: Sharp Laboratories of America (SLA), Inc., Camas, WA (US)

(72) Inventor: Bryan Hallberg, Vancouver, WA (US)

(73) Assignee: LACAMAS LIFE SCIENCES, INC., Camas, WA (US)

( * ) Notice: Subject to any disclaimer, the term of this patent is extended or adjusted under 35 U.S.C. 154(b) by 34 days.

(21) Appl. No.: 14/951,169

(22) Filed: Nov. 24, 2015

(65) Prior Publication Data
US 2017/0143265 A1    May 25, 2017

(51) Int. Cl.
| | |
|---|---|
| A61B 5/00 | (2006.01) |
| A61B 5/021 | (2006.01) |
| A61B 5/022 | (2006.01) |
| A61B 5/024 | (2006.01) |
| A61B 5/0408 | (2006.01) |

(52) U.S. Cl.
CPC ........ *A61B 5/6843* (2013.01); *A61B 5/02416* (2013.01); *A61B 5/0408* (2013.01); *A61B 5/7221* (2013.01); *A61B 5/7246* (2013.01); *A61B 5/7475* (2013.01)

(58) Field of Classification Search
None
See application file for complete search history.

(56) References Cited

U.S. PATENT DOCUMENTS

| | | | |
|---|---|---|---|
| 8,290,730 | B2 | 10/2012 | Watson et al. |
| 8,478,389 | B1 | 7/2013 | Brockwat et al. |
| 8,792,949 | B2 | 7/2014 | Baker |
| 9,005,129 | B2 | 4/2015 | Venkatrman et al. |
| 2012/0253156 | A1* | 10/2012 | Muhlsteff .......... A61B 5/02416 600/324 |

* cited by examiner

*Primary Examiner* — Brian T Gedeon
(74) *Attorney, Agent, or Firm* — Steve Reiss; ScienBiziP, P.C.

(57) ABSTRACT

A system and method are provided for determining sensor contact in a multi-sensor device. The method measures a series of photoplethysmography (PPG) heart beat signals, while simultaneously measuring a series of electrocardiogram (ECG) heart beat signals. The method detects a correlation in time between each of a plurality of PPG signals and corresponding ECG signals. In response to the timing between correlated PPG and ECG signals remaining within a first correlation deviation limit, a correlation state is determined. For example, a correlation state may be determined in response to n out of m number of correlated PPG and ECG signals remaining within the correlation deviation limit, where n and m are integers greater than zero.

20 Claims, 16 Drawing Sheets

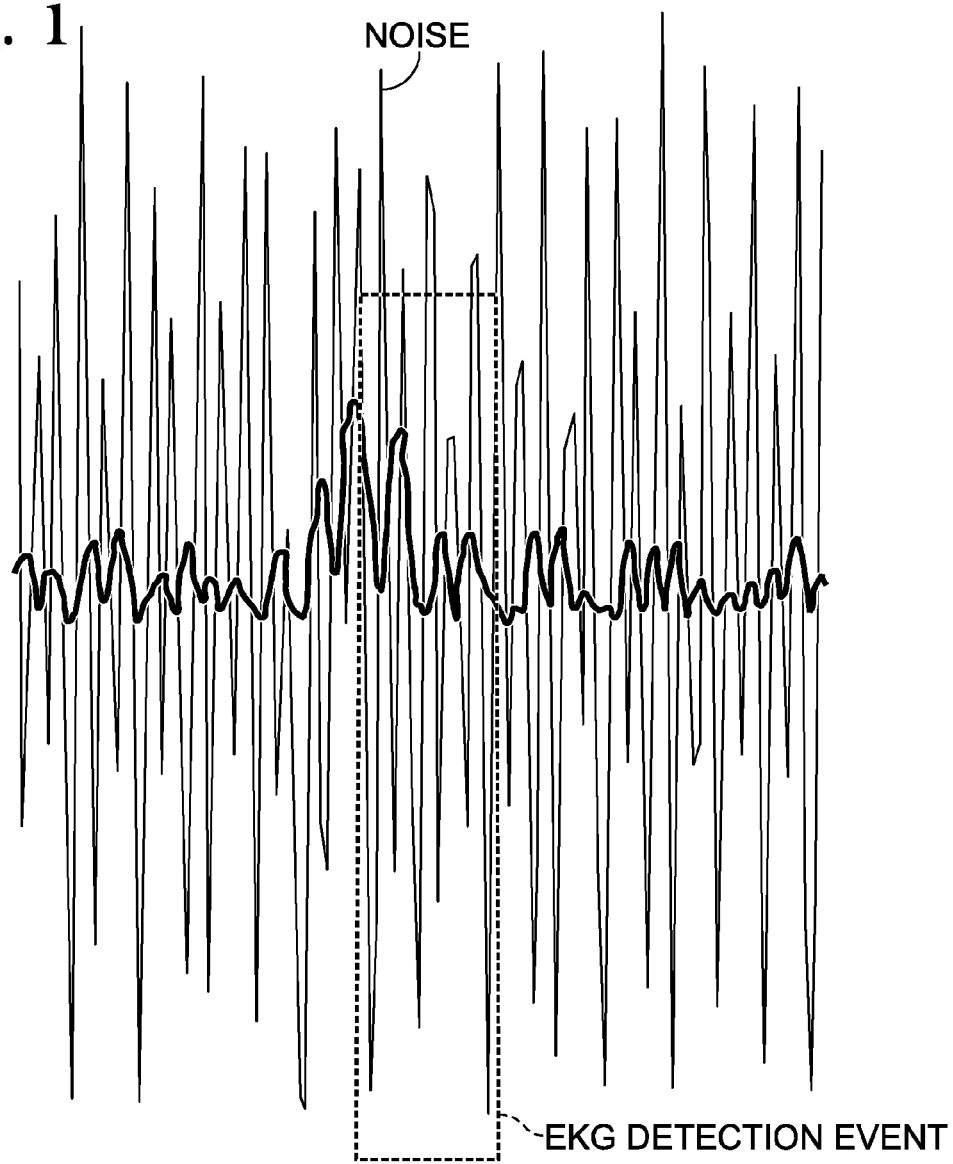
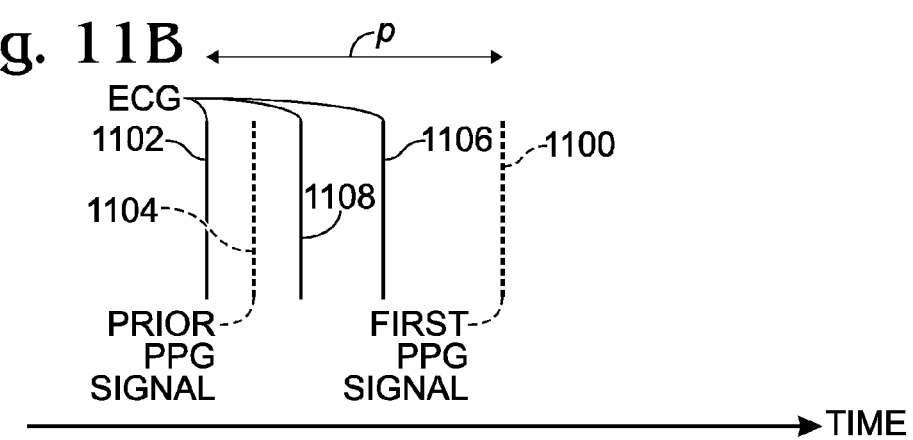

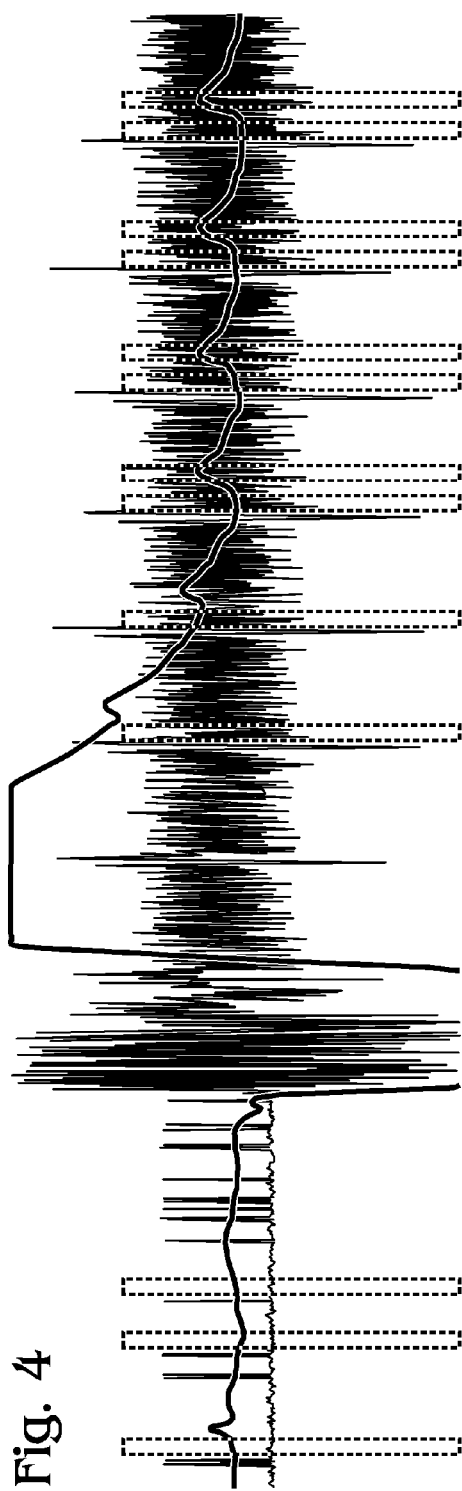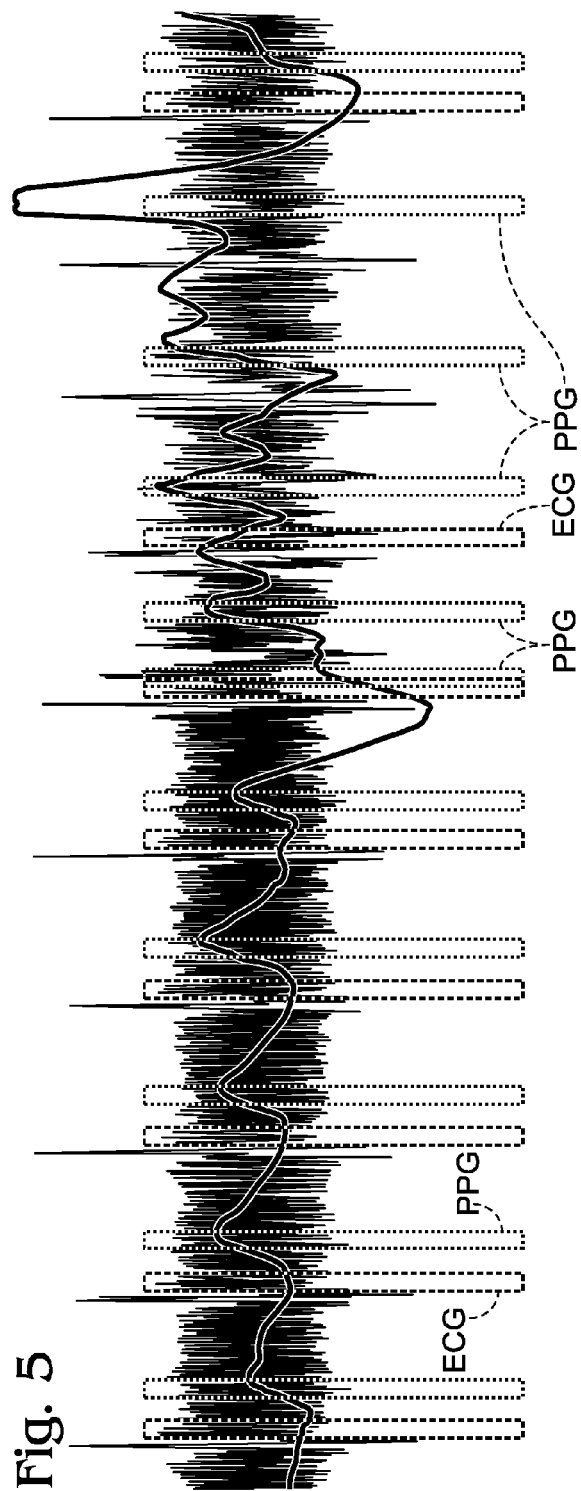

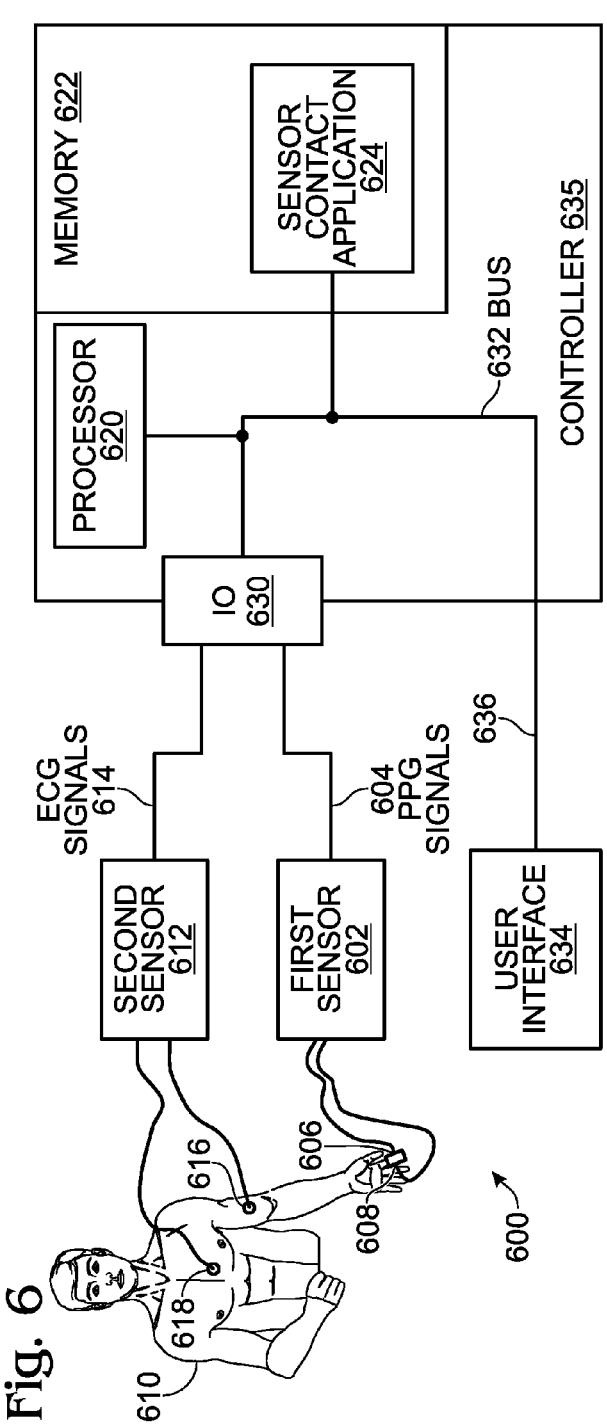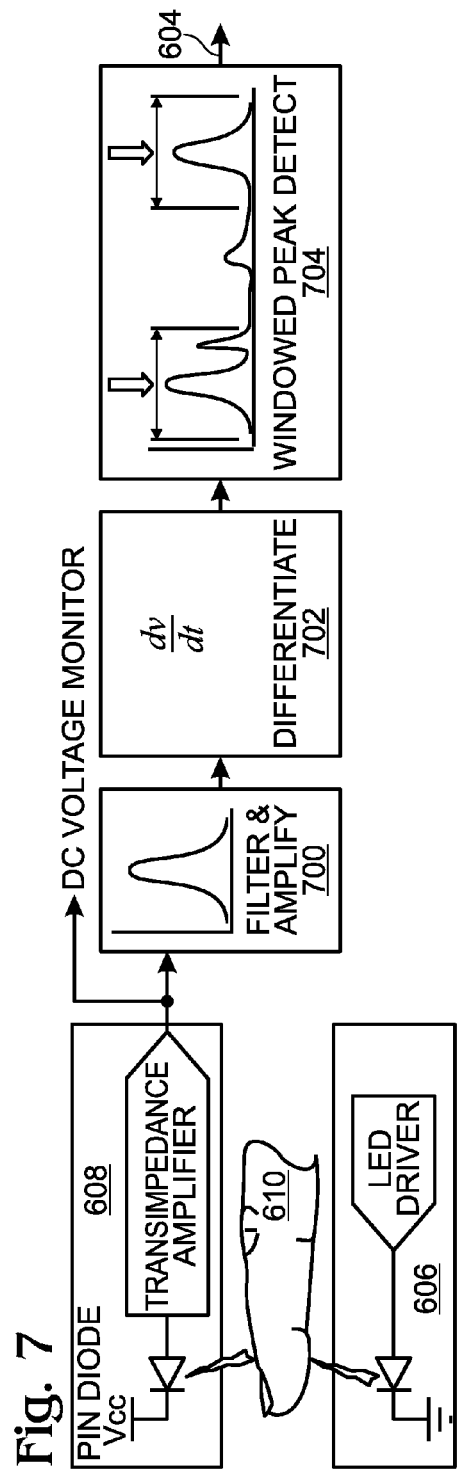

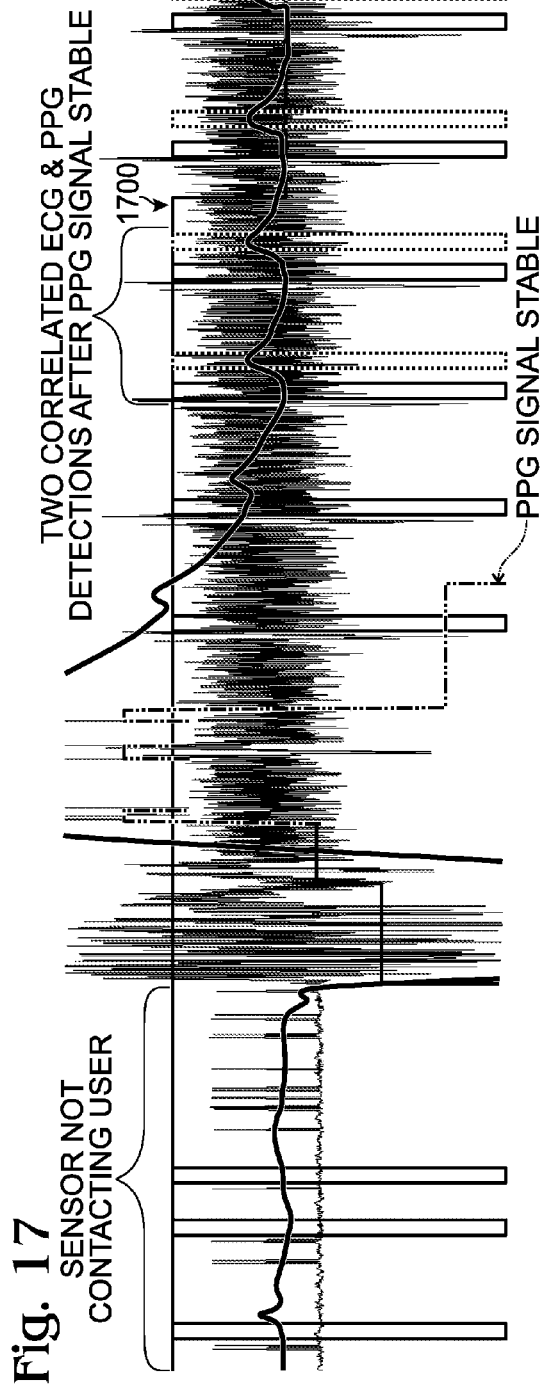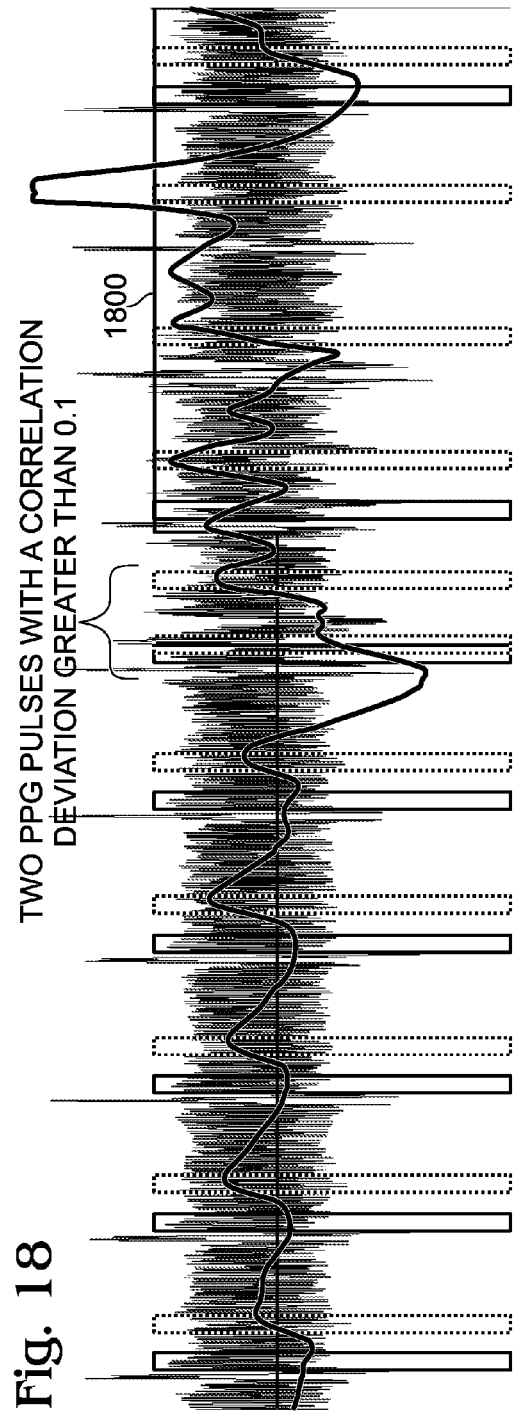

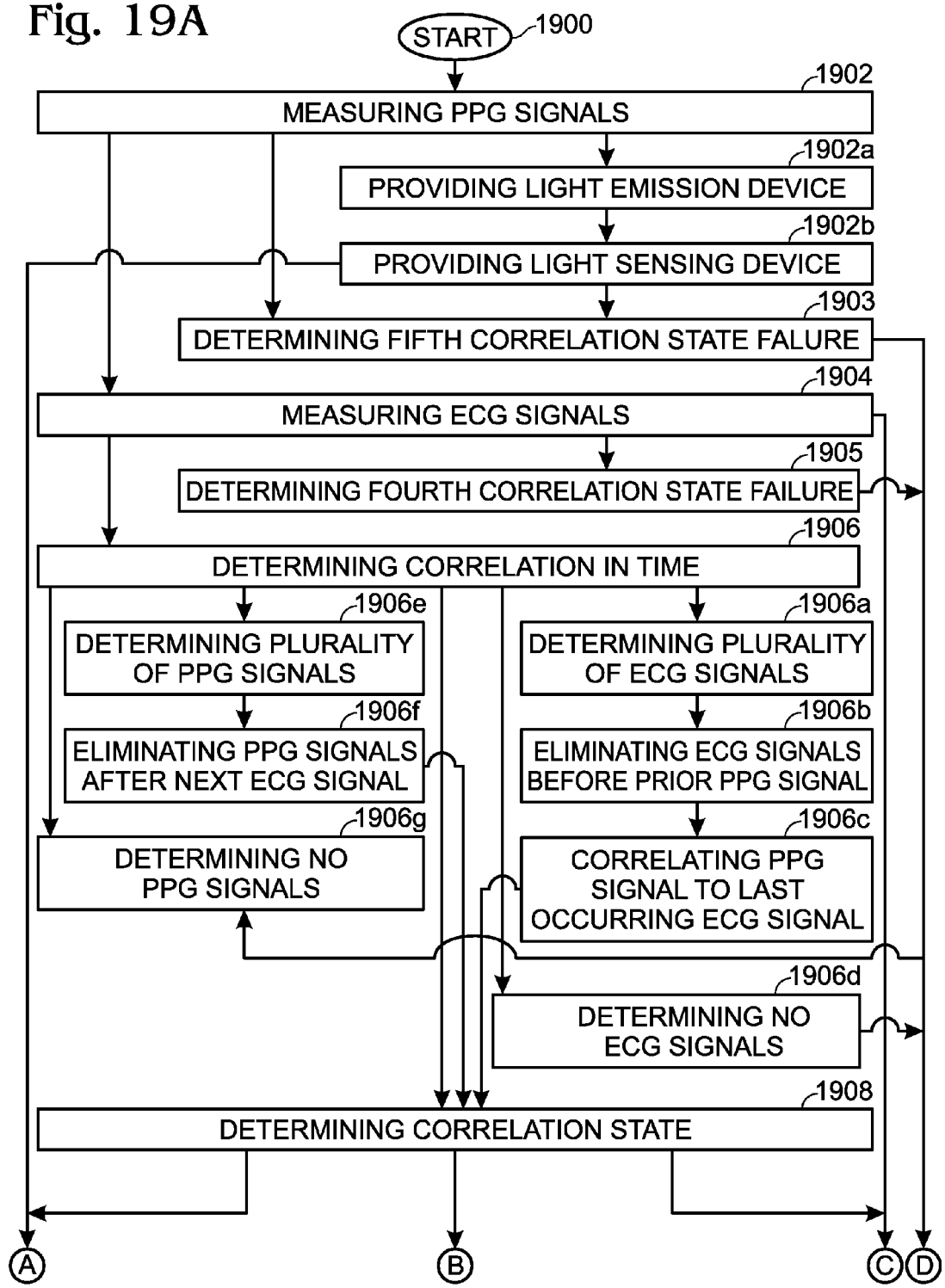

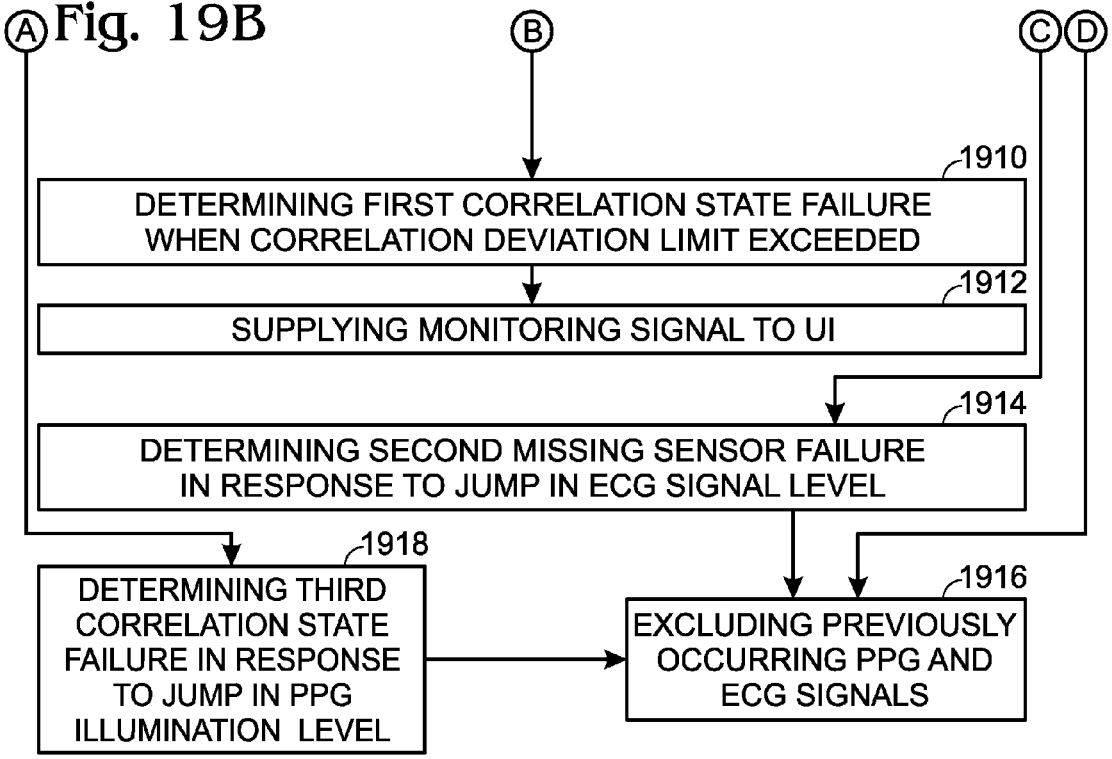

SYSTEM AND METHOD FOR DETERMINING POOR SENSOR CONTACT IN A MULTI-SENSOR DEVICE

BACKGROUND OF THE INVENTION

1. Field of the Invention

This invention generally relates to health monitoring and, more particularly, to a system and method for determining when vital sign monitoring sensors are making poor contact with a patient being monitored.

2. Description of the Related Art

Electrocardiography (ECG or EKG) is the process of recording the electrical activity of the heart over a period of time using electrodes placed on a patient's body. These electrodes detect the tiny electrical changes on the skin that arise from the heart muscle depolarizing during each heartbeat. During each heartbeat, a healthy heart has an orderly progression of depolarization that starts with pacemaker cells in the sinoatrial node, spreads out through the atrium, passes through the atrioventricular node down into the bundle of His and into the Purkinje fibers spreading down and to the left throughout the ventricles. This orderly pattern of depolarization gives rise to the characteristic EC tracing.

A photoplethysmogram (PPG) is an optically obtained plethysmogram, a volumetric measurement of an organ. A PPG is often obtained by using a pulse oximeter which illuminates the skin and measures changes in light absorption. A conventional pulse oximeter monitors the perfusion of blood to the dermis and subcutaneous tissue of the skin. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak. The change in volume caused by the pressure pulse is detected by illuminating the skin with the light from a light-emitting diode (LED) and then measuring the amount of light either transmitted or reflected to a photodiode. Each cardiac cycle appears as a peak.

Current ECG systems typically use wet electrodes and can detect a lead off condition by either measuring the signal noise level or measuring the impedance between the electrodes by periodically passing a small current between them. For wet electrodes on a patient's chest, the expected signal amplitude is known and noise levels are relatively small. Therefore, detecting unexpected noise typical of a lead off condition is relatively easy.

Consumer grade devices uses dry electrodes and they can be placed at numerous different locations on the user's body. Signal levels vary greatly and are dependent upon sensor location and skin dryness. Typically, the noise level can be 10 times greater or more than the signal level.

FIG. 1 is a magnified view of one ECG pulse as measured by a sensor with two dry electrodes. The thicker trace represents the ECG signal after filtering and rectification. Detecting an ECG poor contact condition when using dry ECG electrodes placed in positions with signals as low as those measured on the forehead is particularly challenging. Prior to filtering, valid ECG signals are almost completely masked by environmental noise. Also, a valid signal looks very similar to a poor contact condition.

FIG. 2 is a view representing the measurement of ECG and PPG pulses. In a healthy patient, when the sensors are making proper contact, a PPG pulse should follow each ECG pulse by approximately 250 milliseconds, which is about the time it takes blood to flow from the heart to an extremity plus the pre-ejection period time (PEP), PEP being the time between when the ECG signal peaks and the heart muscle contracts. If the PPG signal is lost, as shown, an alarm should be raised. A similar type alarm should be raised if the ECG signals are lost. The loss of these may indicate that a sensor has been removed.

FIG. 3 is a view representing a condition where environmental noise causes erroneous ECG detection. This condition becomes a problem when the environmental noise has characteristics similar to valid ECG pulses, and so cannot be filtered out.

FIG. 4 is a view of poor sensor contact resulting from the recent placement of the sensor. Recent sensor placement causes poor ECG and PPG event detection since the sensors are not yet stable.

FIG. 5 is a view depicting the lack of temporal correlation between ECG and PPG signals. This lack of correlation in a healthy patient may occur as a result poor sensor contact.

Since valid and invalid ECG signals look very similar, simply measuring the signal to noise ratio does not give a good indication of the poor contact condition. Large amounts of environmental noise can also cause false detections, and low signal quality can cause valid heart pulses to be missed. So, algorithms which only check for the existence or lack of detected pulses have poor contact quality detection in large noise environments.

It would be advantageous if more sophisticated detection processes existed that could determine when ECG and PPG signal errors are the result of poor sensor contact.

SUMMARY OF THE INVENTION

Described herein are systems and methods for detecting poor sensor contact in a vital sign measurement system that measures both ECG (electrocardiogram) and PPG (photoplethysmography) signals. The method can detect if either of the sensors, or both of the sensors, are not making good contact with the user. If a sensor is not making good contact, then the related vital sign measurement will also have poor quality, as the system receives significant noise. The method receives signal status indicators from the ECG and PPG subsystems and combines and correlates those indicators to determine the quality of the contact that the sensors are making with the user. These indicators may include large noise conditions and variations in pulse detection times. Thus, combining ECG and PPG signal indicators helps determines the quality of ECG and PPG sensor contact with the user. Correlating ECG and PPG pulse detection timing information also determines the quality of the sensor contact condition.

Accordingly, a method is provided for determining sensor contact in a multi-sensor device. The method measures a series of PPG heart beat signals, while simultaneously measuring a series of electrocardiogram ECG heart beat signals. The method detects a correlation in time between each of a plurality of PPG signals and corresponding ECG signals. In response to the timing between correlated PPG and ECG signals remaining within a first correlation deviation limit, a correlation state is determined. For example, a correlation state may be determined in response to n out of m number of correlated PPG and ECG signals remaining within the correlation deviation limit, where n and m are integers greater than zero. In one aspect, the number of m signals is the larger of a first predetermined number (a) or a calculated number. The calculated number is equal to the smaller of a second predetermined number (b), or the number of measured ECG signals, or the number of measured PPG signals.

In another aspect, the correlation in time is detected by correlating a leading edge of a first PPG signal to a previous ECG R-wave occurring no more than p milliseconds before the first PPG signal, where p is a value greater than zero. In one circumstance, when a plurality of previous ECG signals are measured that occur no more than p milliseconds before the first PPG signal, all the signals occurring before a prior PPG signal (occurring before the first PPG signal) are eliminated. Then, the first PPG signal is correlated to the last occurring ECG signal in the plurality of previous ECG signals. However, if there are no ECG signals occurring within p milliseconds of the first PPG signal, the method determines that the correlation deviation limit associated with the first PPG signal has been exceeded.

In a different scenario, the correlation in time is detected by measuring a plurality of subsequent PPG signals occurring no more than p milliseconds subsequent to a first ECG signal. All PPG signals occurring subsequent to a second ECG signal are eliminated, when the second ECG signal occurs subsequent to the first ECG signal. However, if there are no subsequent PPG signals following the first ECG signal, the method determines that the correlation deviation limit associated with the first ECG signal has been exceeded.

After determining that a correlation state exists, if less than x out of y number of correlated PPG and ECG signals occur within the correlation deviation limit, where x and y are integers greater than zero, the method determines a first correlation state failure. In one aspect, the number of y signals is the larger of a first predetermined number (c) or a calculated number. The calculated number is equal to the smaller of a second predetermined number (d), or the number of measured ECG signals, or the number of measured PPG signals.

In another aspect, if a subsequent EC signal level exceeds the immediately previous detection threshold level by a factor of r, where r is a value greater than zero, the method determines a second missing sensor failure and excludes all previously occurring ECG and PPG signals from subsequent correlation state determinations. Similarly, if the light sensing device of the PPG sensor detects a change of illumination greater than within a predetermined time period, where z is a value greater than zero, the method determines a third correlation state failure and excludes all previously occurring ECG and PPG signals from subsequent correlation state determinations. If there is a failure to measure either ECG or PPG signals within a predetermined period of time, a correlation state failure is declared and all previously occurring ECG and PPG signals are excluded from subsequent correlation state determinations.

Additional details of the above-described method and a system for determining sensor contact in a multi-sensor device are provided below.

BRIEF DESCRIPTION OF THE DRAWINGS

FIG. 1 is a magnified view of one ECG pulse as measured by a sensor with two dry electrodes.

FIG. 4 is a view of poor sensor contact resulting from the recent placement of the sensor.

FIG. 5 is a view depicting the lack of temporal correlation between ECG and PPG signals.

FIG. 6 is a schematic block diagram of a system for determining sensor contact in a multi-sensor device.

FIG. 7 is a schematic block diagram depicting an exemplary first (PPG) sensor subsystem.

FIGS. 11A through 11C are drawings depicting the relationship between corresponding ECG and PPG signals.

FIG. 17 is a plot depicting poor ECG contact following recent sensor placement.

FIG. 18 is a plot depicting uncorrelated pulse detection.

FIGS. 19A and 19B are flowcharts illustrating a method for determining sensor contact in a multi-sensor device.

DETAILED DESCRIPTION

Figure 2:
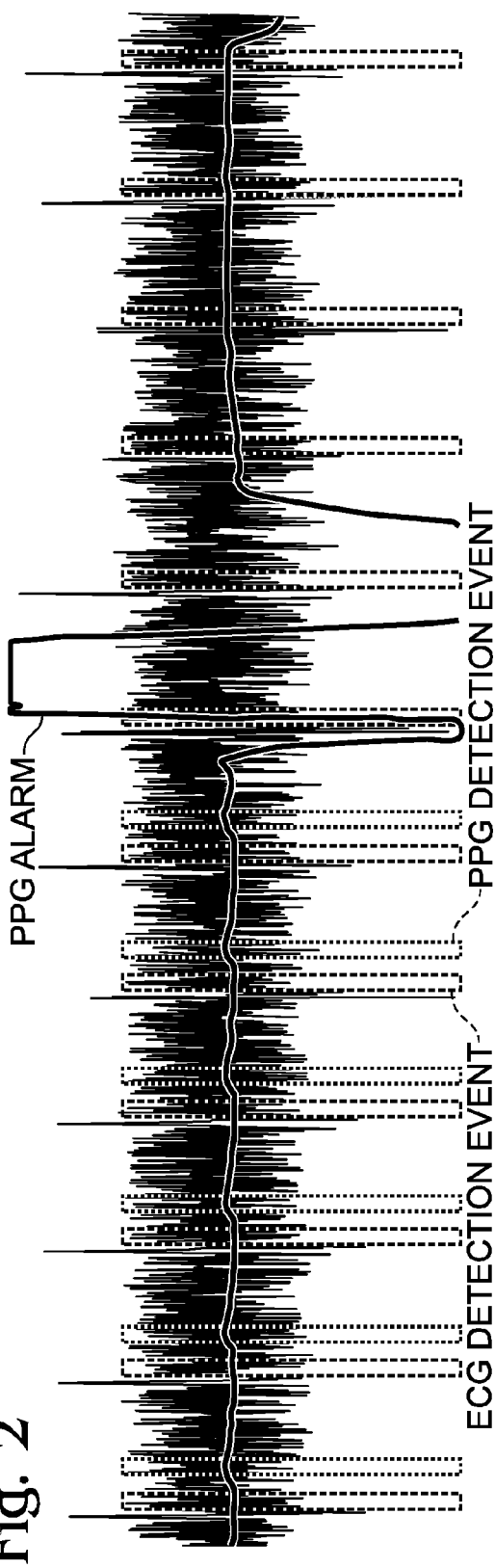
FIG. 2 is a view representing the measurement of ECG and PPG pulses.
Figure 3:
FIG. 3 is a view representing a condition where environmental noise causes erroneous ECG detection.

FIG. 6 is a schematic block diagram of a system for determining sensor contact in a multi-sensor device. The system 600 comprises a first sensor 602 having an output on line 604 to supply measured photoplethysmography (PPG) signals. Typically, the first (PPG) sensor 602 comprises a light emission device 606 and a light sensing device 608 for detecting changes in an optical transmittance of an illuminated test subject body 610. A second sensor 612 has an output on line 614 to supply measured electrocardiogram (ECG) signals. Typically, the second (ECG) sensor 612 comprises at least two electrodes 616 and 618.

The system 600 further comprises a processor 620 and a non-transitory memory 622. A sensor contact application 624 resides in the non-transitory memory 622 and comprises a sequence of processor instructions. The sensor contact application 624 receives the PPG and ECG signals, detects a correlation in time between PPG signals and corresponding ECG signals. The ECG and PPG measurements may be passed through an input/output (IO) port 630, and operatively connected to the processor 620 and sensor contact application 624 via bus 632. If the timing between correlated PPG and ECG signals remains within a correlation deviation limit, the sensor contact application 624 determines a correlation state. In one aspect, the system comprises a user interface (UI) 634 having an input connected to the sensor contact application on line 636 for accepting a signal responsive to the relationship between n and m, and an output to present the relationship between n and m.

The combination of the processor 620, memory 622, sensor contact application 624, bus 632, IO port 630, and UI 634 may be referred to as a computing device or controller 635. The communication bus 632 may, for example, be a Serial Peripheral interface (SPI), an Inter-Integrated Circuit ($I^2C$), a Universal Asynchronous Receiver/Transmitter (UART), and/or any other suitable bus or network. Although the drawing implies that the components of the controller 635 are collocated in the same device, in some aspects various components may be located outside the device, communicating with other components via a hardwire or wireless connection.

The memory 622 may include a main memory, a random access memory (RAM), or other dynamic storage devices. These memories may also be referred to as a computer-readable medium. Such a medium may take many forms, including but not limited to, non-volatile media, volatile media, and transmission media. Non-volatile media includes, for example, optical or magnetic disks. Volatile media includes dynamic memory. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, or any other medium from which a computer can read. The execution of the sequences of instructions contained in a computer-readable medium (i.e. sensor contact application 624) may cause the processor 620 to perform some of the steps of determining sensor contact. Alternately, some of these functions may be performed in hardware (not shown). The practical implementation of such a computer system would be well known to one with skill in the art. In one aspect, the processor 620 is a 16-bit microcontroller or an ARM processor using a reduced instruction set computing (RISC) architecture.

The user interface 634 and IO port 630 may incorporate a display, a modem, an Ethernet card, or any other appropriate data communications device such as USB. The physical communication links may be optical, wired, or wireless. The user interface 634 may incorporate a keypad or a cursor control device such as a mouse, touchpad, touchscreen, trackball, stylus, or cursor direction keys.

The controller 635 may be considered a type of special purpose computing system, and as such, can be programmed, configured, and/or otherwise designed to comply with one or more networking protocols. According to certain embodiments, the controller 635 may be designed to work with protocols of one or more layers of the Open Systems Interconnection (OSI) reference model, such as a physical layer protocol, a link layer protocol, a network layer protocol, a transport layer protocol, a session layer protocol, a presentation layer protocol, and/or an application layer protocol. For example, IO 630 may include a network device configured according to a Universal Serial Bus (USB) protocol, an Institute of Electrical and Electronics Engineers (IEEE) 1394 protocol, an Ethernet protocol, a T1 protocol, a Synchronous Optical Networking (SONET) protocol, a Synchronous Digital Hierarchy (SDH) protocol, an Integrated Services Digital Network (ISDN) protocol, an Asynchronous Transfer Mode (ATM) protocol, a Point-to-Point Protocol (PPP), a Point-to-Point Protocol over Ethernet (PPPoE), a Point-to-Point Protocol over ATM (PPPoA), a Bluetooth protocol, an IEEE 802.XX protocol, a frame relay protocol, a token ring protocol, a spanning tree protocol, and/or any other suitable protocol.

The controller 635 may provide a direct connection to a remote server via a direct link to a network, such as the Internet. Connection may be provided through, for example, a local area network (such as an Ethernet network), a personal area network, a wide area network, a private network (e.g., a virtual private network), a telephone or cable network, a cellular telephone connection, a satellite data connection, or any other suitable connection.

In certain embodiments, a host adapter is configured to facilitate communication between controller 635 and one or more network or storage devices via an external bus or communications channel. Examples of host adapters include, without limitation, Small Computer System Interface (SCSI) host adapters, Universal Serial Bus (USB) host adapters. IEEE 1394 host adapters, Advanced Technology Attachment (ATA). Parallel ATA (PATA), Serial ATA (SATA), and External SATA (eSATA) host adapters, Fibre Channel interface adapters, Ethernet adapters, or the like.

It is possible to attach ECG sensor electrodes 616 and 618 to many possible test subject (patient) body locations, and the strength and validity of the ECG signals is sensitive to the locations selected. Thus, the UI 634 may have an input (e.g., a keypad) for accepting information concerning test subject body locations and an output for supplying the information to the sensor contact application. As a result, the sensor contact application 624 may determine the correlation state by modifying the ratio of n to m in response the body locations selected for the ECG signal measurement.

FIG. 7 is a schematic block diagram depicting an exemplary first (PPG) sensor subsystem. After the light sensing device 608 detects a change in illumination, the detected signal is filtered and amplified at block 700, differentiated at block 702, and compared against a threshold at block 704.

The subsystem uses a dynamically adjusted voltage threshold level which is compared against an amplified, filtered, and differentiated version of the received raw PPG waveform. Only differential results greater than zero are used, since the goal is to locate the fastest rising leading edge. The threshold is set to be a fraction of the typical recent tallest signal levels. The tallest peak above the threshold in a predetermined time window is considered to be a PPG pulse. More sophisticated algorithms also check that too many tall peaks do not occur within the window, as this would be an indication of noise. The window width is based upon the maximum expected heart rate. For example, a maximum rate of 180 would mean that all smaller pulses within 330 milliseconds (60 seconds/180) of the tallest pulse would be considered invalid PPG pulses. PPG systems typically adjust the brightness of the sensor LED. The PPG signal is considered stable a short amount of time after the brightness adjustment stops, because any adjustment of the light affects the received signal shape. Typically this time is 1 to 2 seconds, based upon the characteristics of the filter used in the system.

Figure 8:
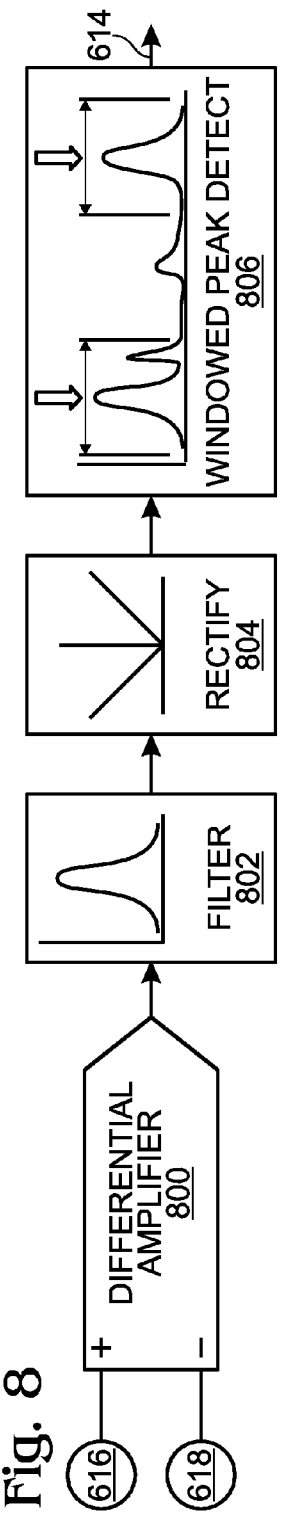
FIG. 8 is a schematic block diagram depicting an exemplary second (ECG) sensor subsystem.

FIG. 8 is a schematic block diagram depicting an exemplary second (ECG) sensor subsystem. After electrodes 616 and 618 detect a signal, it is differentially amplified at block 800, filtered at block 802, rectified at block 804, and compared against a threshold in block 806. More sophisticated subsystems may use several electrodes.

The subsystem uses a dynamically adjusted voltage threshold level which is compared against an amplified, filtered, and rectified version of the received raw ECG waveform. The threshold is set to be a fraction of the typical recent tallest signal levels. The tallest peak above the threshold in a predetermined time window is considered to be an ECG pulse. More sophisticated algorithms also check that too many tall peaks do not occur within the window, as this would be an indication of noise. The window width is based upon the maximum expected heart rate. For example, a maximum rate of 180 would mean that all smaller pulses within 330 milliseconds (60 seconds/180) of the tallest pulse would be considered invalid ECG pulses.

Figure 9A:
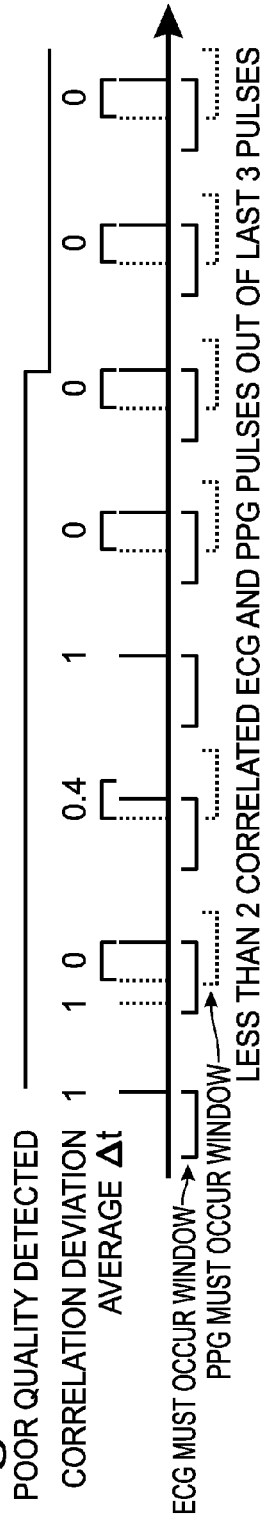
FIGS. 9A and 9B are plots of ECG and PPG measurements illustrating some rules of correlation.
Figure 9B:
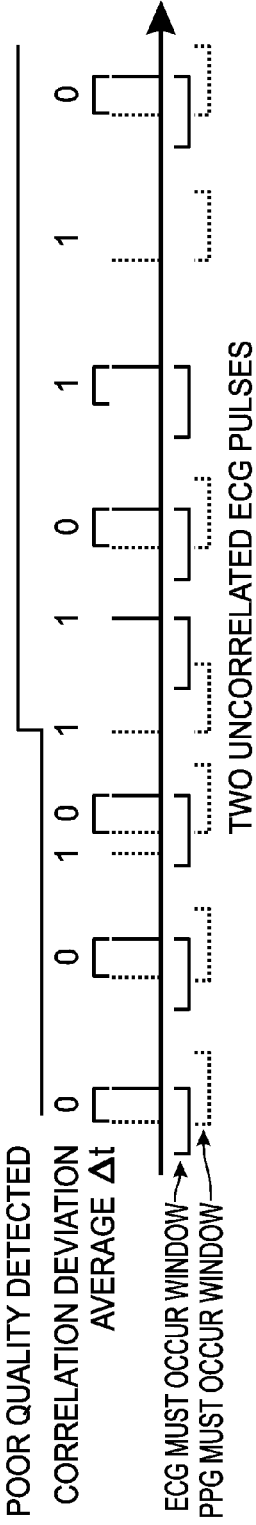

FIGS. 9A and 9B are plots of ECU and PPG measurements illustrating some rules of correlation. FIG. 9A starts with sensor contact in the poor state, which is typical of a power on condition or recently placed sensor condition. In one aspect, while the sensor contact is poor, the sensor contact application determines the correlation state has occurred when n out of m number of correlated PPG and ECG signals occur within the correlation deviation limit, where n and m are integers greater than zero. For example, n may be equal to 2, m equal to 3, and the correlation deviation limit equal to 0.1. The poor quality signal indicator changes from 1 to 0 once 2 of the last 3 ECG and PPG signals have correlation deviations less than 0.1. This scenario is referred to as Rule 1. These rules are discussed in more detail below.

Similarly in FIG. 9B, the sensor contact application, after initially determining the correlation state, determines a first correlation state failure if less than x out of y number of correlated PPG and ECG signals occur within the correlation deviation limit, where x and y are integers greater than zero. This scenario is referred to as Rule 2.

FIGS. 10A through 10D are flowcharts illustrating some additional correlation scenarios. The values of m (or n) do not necessarily have to remain static. In one aspect, the number of m signals is the larger of two numbers in a first set of numbers, where the first set contains a first predetermined number (a) and a calculated number, and where the calculated number is the smaller of three numbers in a second set of numbers. The second set contains a second predetermined number (b), the number of measured ECG signals, and the number of measured PPG signals. These rules are explicitly depicted in Step 1082 in FIG. 10D, where the value "2" is the first predetermined number and the value "3" is the second predetermined number.

Figure 10A:
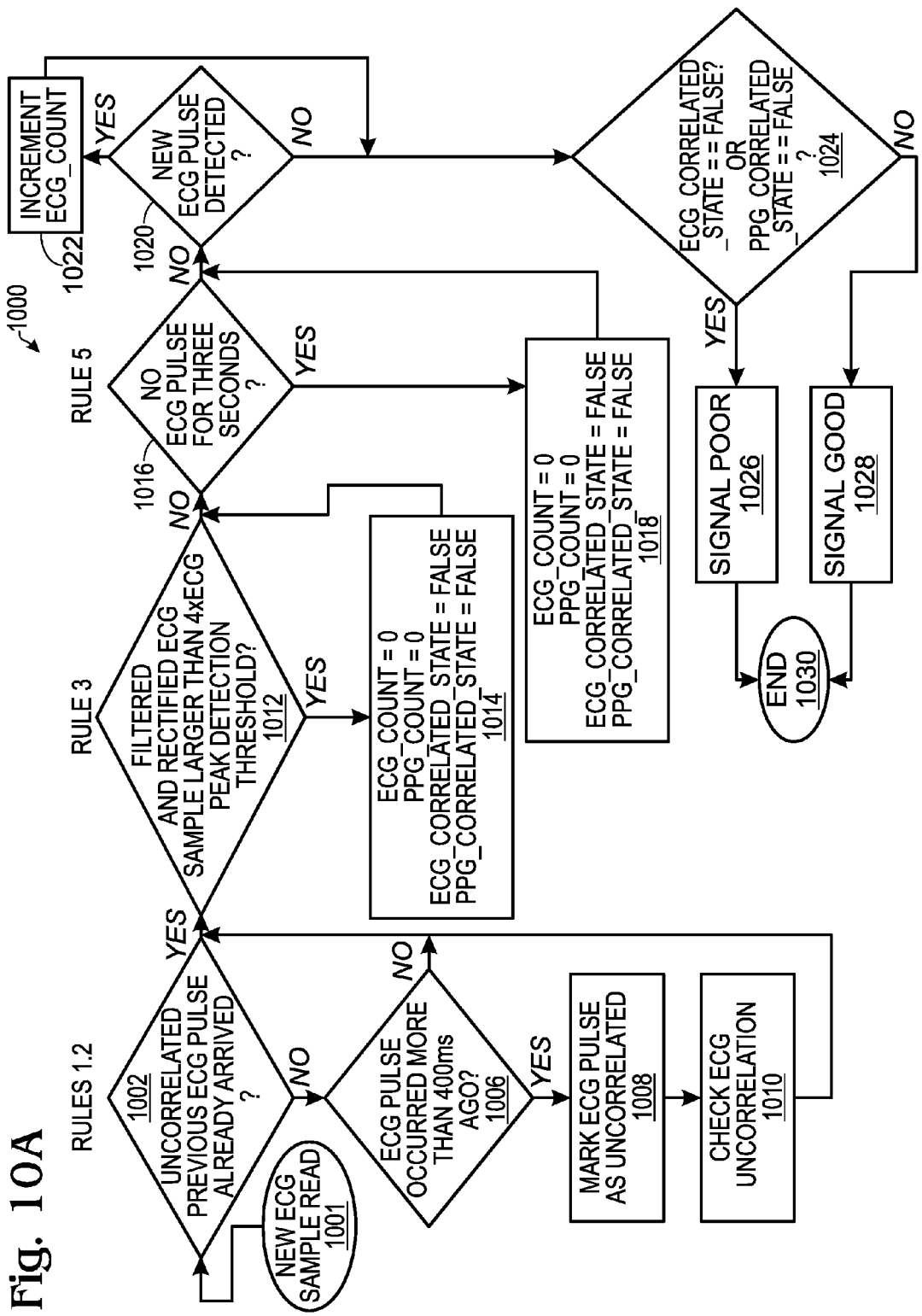
FIGS. 10A through 10D are flowcharts illustrating some additional correlation scenarios.
Figure 10B:
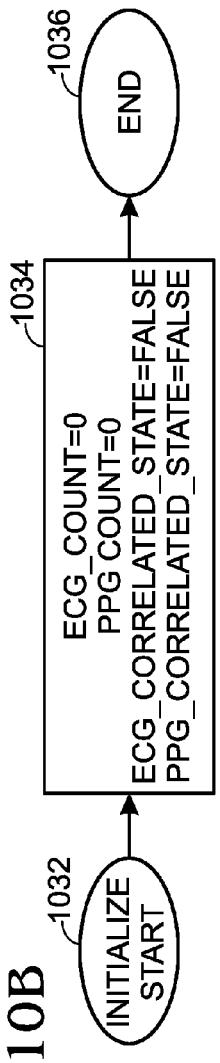

The system powers up (Step 1032, FIG. 10B) with the correlation detection variables set to their reset states of the ECG and PPG counts equaling zero and their correlation states set to false (Step 1034), and power up ends in Step 1036. ECG and PPG samples arrive into the system and are processed by ECG flowchart 1000 (FIG. 10A). PPG flowchart 1040, and Correlation flowchart 1072 shown in FIGS. 10A, 10C, to 10D. For example, a typical system sample rate may be 250 Hz, so both the ECG and the PPG flowcharts are called at the 250 Hz rate, each of which may subsequently call the Correlation flowchart.

As each ECG sample arrives, it enters the ECG flowchart 1000 at Step 1001, causing the entire ECG flowchart to be evaluated. Step 1002 checks whether an EC pulse previous to the current sample had been previously detected by the system and if that ECG pulse is not yet correlated with a PPG pulse. If no uncorrelated ECG pulse exists, the processing proceeds to Step 1012. If an uncorrelated ECG pulse does exist, then processing proceeds to Step 1006, which checks whether the pulse occurred more than a first predetermined time (e.g., 400 ms) prior to the current sample. If the pulse occurred less than the first predetermined time ago, then processing again proceeds to Step 1012. Otherwise, processing proceeds to Step 1008 and the ECG pulse is marked as uncorrelated, by setting its correlation deviation to 1. Next, Step 1010 calls Correlation flowchart 1072 to determine if the ECG signal is still correlated. Flowchart 1072 is described below. Processing of the current ECG sample then proceeds to step 1012.

Step 1012 evaluates Rule 3, checking for significant noise in the ECG signal. If the ECG signal level is less than a factor r (typically 4) of a threshold level, then the signal is considered to be below the noise threshold and processing proceed to Step 1016. Otherwise, the signal does contain noise and processing proceeds to Step 1014. The threshold level is set in Step 1020 during ECG pulse detection. Step 1014 sets the correlation detection variables to their reset state. Processing then proceeds to Step 1016.

Step 1016 evaluates Rule 5, checking for a lack of ECG pulses. If at least one ECG pulse has been detected within a second predetermined time (e.g., 3 seconds) prior to the current sample, then processing proceeds to Step 1020. Otherwise, processing proceeds to Step 1018, which sets the correlation detection variables to their reset state. Processing then proceeds to Step 1020.

Step 1020 checks for detection of a new ECG pulse. An exemplary ECG detection system is shown in FIG. 8. If no new ECG pulse is detected, then processing proceeds to Step 1024. Otherwise, processing proceeds to Step 1022, which increments the ECG pulse detection counter. Processing then proceeds to Step 1024.

Step 1024 checks if either the ECG or PPG correlated states are false. If either is false, then processing proceeds to Step 1026 which sets the signal quality state to poor. Otherwise, processing proceeds to Step 1028 which sets the signal quality state to good. Processing the current ECG sample is then concluded as the flowchart terminates at Step 1030.

As each PPG sample arrives, it enters the PPG flowchart 1040 at Step 1041, causing the entire PPG flowchart to be evaluated. Step 1042 checks for detection of a new PPG pulse. An exemplary PPG detection system is shown in FIG. 7. If no new PPG pulse is detected, then processing proceeds to Step 1052. Otherwise, processing proceeds to Step 1044, which increments the PPG pulse detection counter. Next, Step 1046 checks whether a not yet correlated ECG pulse previous to the newly detected PPG pulse occurred within the first predetermined time prior to the current sample. If an uncorrelated ECG pulse in that time period exists, then the correlation deviation for the ECG/PPG pair is evaluated and processing proceeds to Step 1050. Otherwise, processing proceeds to Step 1048 and the PPG pulse is marked as uncorrelated, by setting its correlation deviation to 1. Next, Step 1050 calls Correlation flowchart 1072 to determine if the PPG signal is still correlated. Flowchart 1072 is described below. Processing of the current PPG sample then proceeds to Step 1052.

Step 1052 evaluates Rule 4, checking for significant noise in the PPG signal. If the PPG signal corresponds to an illumination change less than a percentage z (typically 5%) of its full scale signal, then the signal is considered to be below the noise threshold and processing proceed to Step 1056. Otherwise, the signal does contain noise and processing proceeds to Step 1054. Step 1054 sets the correlation detection variables to their reset state. Processing then proceeds to Step 1056.

Step 1056 evaluates Rule 6, checking for a lack of PPG pulses. If at least one PPG pulse has been detected within the second predetermined time prior to the current sample, then processing proceeds to Step 1060. Otherwise, processing proceeds to Step 1058, which sets the correlation detection variables to their reset state. Processing then proceeds to Step 1060.

Step 1060 checks if either the ECG or PPG correlated states are false. If either is false, then processing proceeds to Step 1062 which sets the signal quality state to poor. Otherwise, processing proceeds to Step 1068 which sets the signal quality state to good. Processing the current PPG sample is then concluded as the flowchart terminates at Step 1070.

Figure 10D:
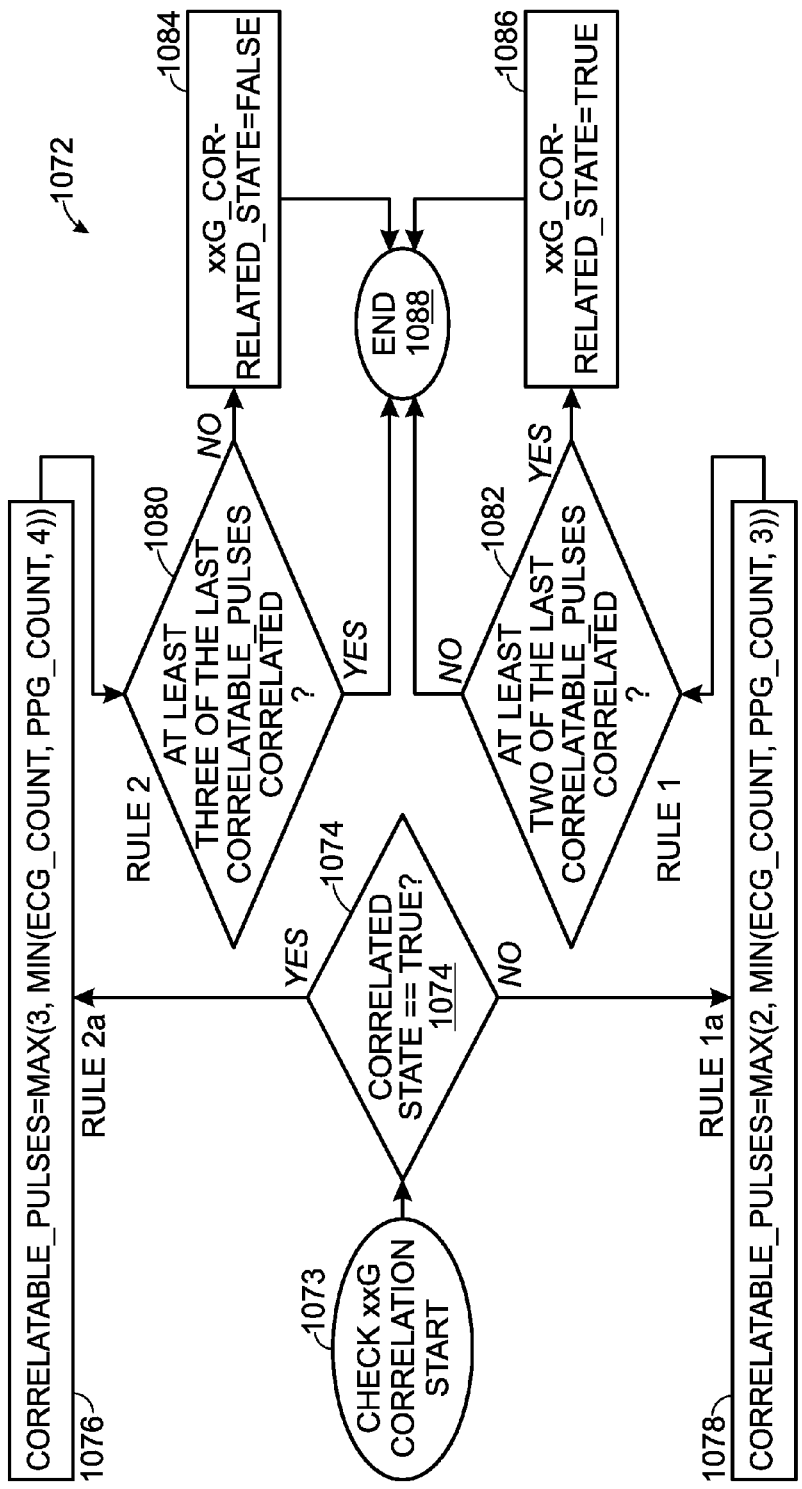
Figure 10C:
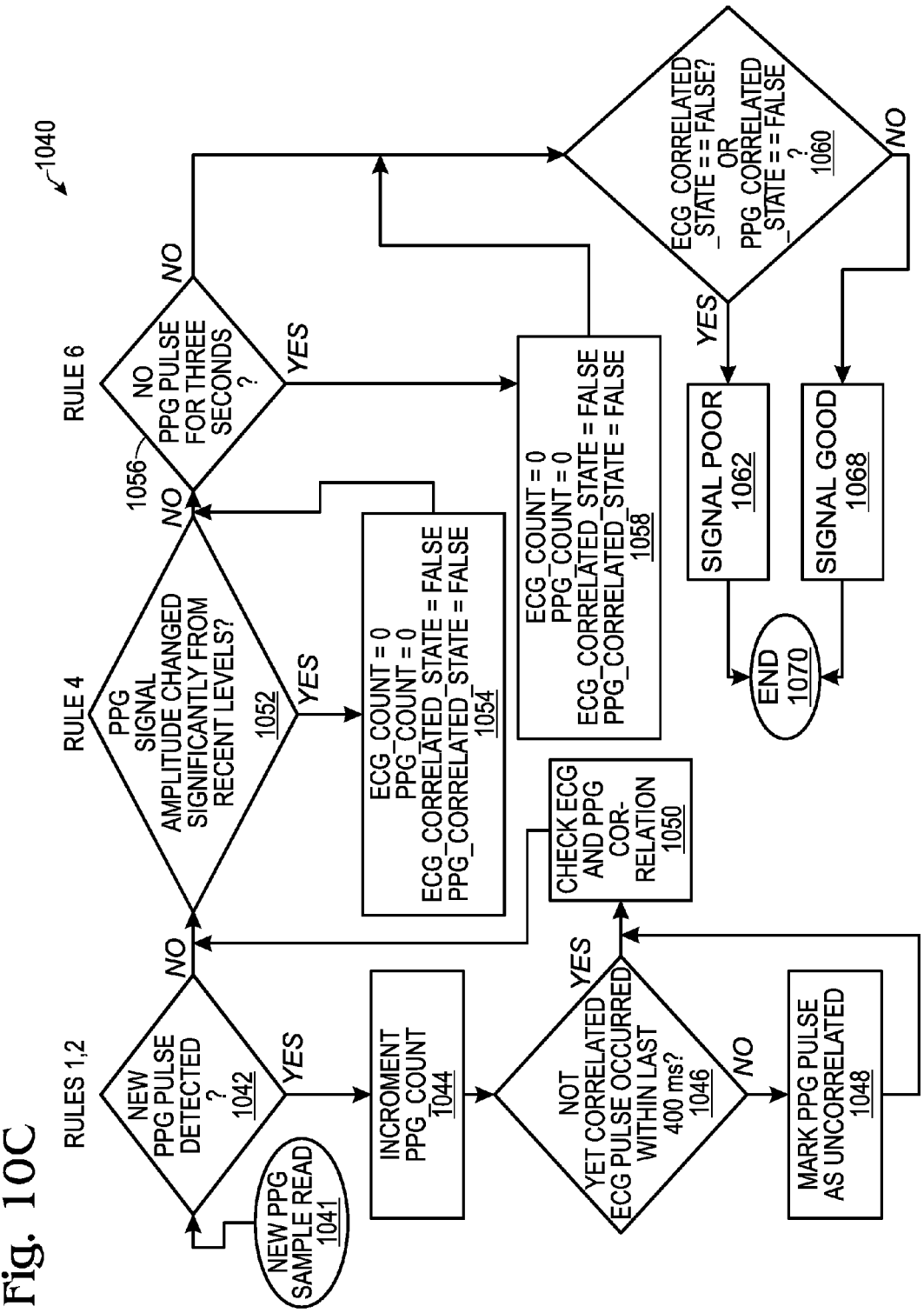

Flowchart 1072, shown in FIG. 10D, illustrates how the global correlation state of a plurality of temporally adjacent ECG and PPG pulses is determined. The flowchart is called from either the ECG or PPG flowcharts and entered starting at Step 1073. Step 1074 checks whether the calling flowchart's correlation state is true. If the correlation state is true, then processing proceeds to Step 1076. Otherwise, it proceeds to Step 1078.

Step 1076 implements Rule 2a and calculates the number, y, of pulses in a plurality of most recent pulses, which will be checked for correlation when the calling flowchart's correlation state is true. Step 1076 calls Step 1080, which implements Rule 2 and determines whether at least the number x of the last y pulses are correlated. If they are correlated, then processing proceeds to Step 1088 which returns processing control to the calling flowchart. Otherwise, processing proceeds to Step 1084 which sets the calling flowchart's correlation state to false. Processing then proceeds to Step 1088.

Step 1076 implements Rule 1a and calculates the number, m, of pulses in a plurality of most recent pulses which will be checked for correlation when the calling flowchart's correlation state is false. Step 1078 calls Step 1082 which implements Rule 1 and determines whether at least the number n of the last m pulses are correlated. If they are not correlated, then processing proceeds to Step 1088. Otherwise, processing proceeds to Step 1086 which sets the calling flowchart's correlation state to true. Processing then proceeds to Step 1088.

Figure 11A:
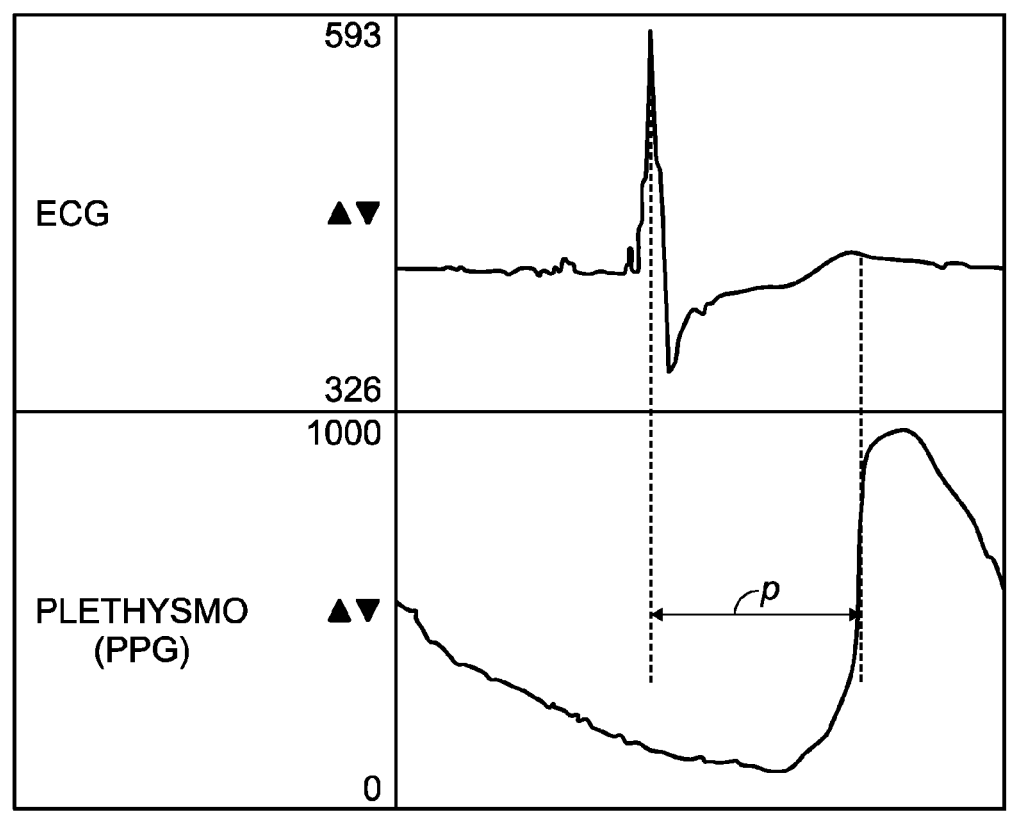
Figure 11C:
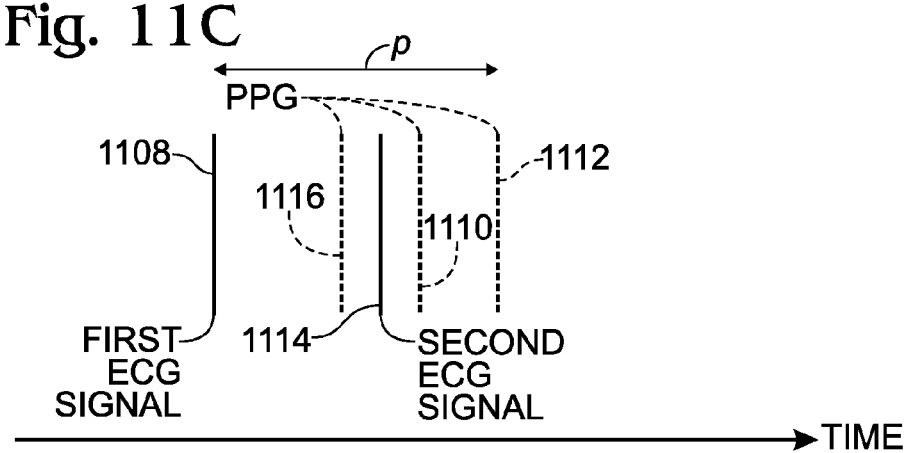

FIGS. 11A through 11C are drawings depicting the relationship between corresponding ECG and PPG signals. The sensor contact application determines the correlation in time by correlating a leading edge of a first PPG signal to a previous ECG R-wave occurring no more than p milliseconds before the first PPG signal, where p is a value greater than zero (FIG. 11A).

The correlation between an ECG and PPG pulse pair is determined by the following rules:

The correlated ECG pulse is the ECG pulse occurring most immediately prior to the PPG pulse within a predetermined amount of time (e.g., 40 milliseconds) before the PPG pulse. The correlation deviation between the ECG and PPG pulses for a well correlated ECG/PPG pair is less than a predetermined amount (e.g., 0.1). The predetermined amount can be set to different values depending upon where the sensors are placed on the body. For example, forehead measurements typically have a correlation deviation of 0.05 while finger measurements typically have a deviation of 0.01. Correlation deviation is calculated by taking the absolute value of one minus the ratio of the difference in the time between the PPG and ECG pulse detection pair and the average difference in time for a predetermined number (e.g., 20) of recently correlated pulses.

$$\text{Correlation Deviation} = \left| 1 - \frac{(T_{PPG} - T_{ECG})}{(T_{PPG} - T_{ECG})} \right|$$

A correlation deviation of zero occurs when the timing difference of the current pair is exactly equal to the average timing difference of the plurality of the recently correlated pulses. The correlation deviation becomes larger as the timing difference becomes larger, and is equal to 1 when the current timing difference is either zero or twice the plurality's average timing difference.

In FIG. 11B the sensor contact application measures a plurality of previous ECG signals occurring no more than p milliseconds before the first PPG signal 1100. All of the previous ECG signals occurring (i.e., ECG signal 1102) before a prior PPG signal 1104 are eliminated. As shown, the prior PPG signal 1104 occurs before the first PPG signal 1100). The first PPG signal 1100 is then correlated to the last occurring ECG signal 1106 in the plurality of previous ECG signals.

Also depicted in FIG. 11B, when ECG signal 1106 was detected, the sensor contact application determined that no PPG signals occurred subsequent to ECG signal 1108 and prior to the ECG signal 1106. The sensor contact application determines that the correlation deviation limit associated with the ECG signal 1108 has been exceeded in response to there being no PPG signals between ECG signals 1106 and 1108.

In FIG. 11C the sensor contact application measures a plurality of subsequent PPG signals occurring no more than p milliseconds subsequent to a first ECG signal 1108. All subsequent PPG signals (i.e., 1110 and 1112) occurring subsequent to a second ECG signal 1114 are eliminated. As shown, the second ECG signal 1114 occurs subsequent to the first ECG signal 1108, and then PPG signal 1116 is correlated with ECG signal 1108.

Also depicted in FIG. 11C, when PPG signal 1112 was detected, the sensor contact application determined that no ECG signals occurred prior to that first PPG signal 1112 and subsequent to any other prior PPG signal (i.e., PPG signal 1110). The sensor contact application then determines that the correlation deviation limit associated with PPG signal 1112 has been exceeded in response to there being no ECG signals between PPG signals 1110 and 1112.

The correlation deviation calculation described above is combined with a set of rules to create a method specifically tailored for a specialized device built to measure ECG and PPG sensor contact failures. An implementation of the method is outlined in flowcharts for FIGS. 10A to 10C. The method's goal is to quickly and reliably determine the quality of the ECG and PPG sensor contact with the user. It is desired to make this determination without the use of additional hardware, such as sending a current through the user to measure impedance. Even when the user is touching both ECG electrodes, the signal may still be of too poor quality to be useful. The poor contact indication should also be made under this situation.

Using the signals available from typical ECG and PPG sensors, poor sensor contact can be detected as described herein. The following set of 6 rules detects the existence of poor sensor contact. The results of each rule are logically OR'ed together to create an overall sensor contact result. Two of the rules, Rule 1 and Rule 2, have sub-rules, Rule 1a and Rule 2a, respectively, that may adjust a parameter used in these rules. The individual rules for detecting poor sensor contact are:

Rule 1: While the current sensor contact status is poor, if more than a predetermined number, m·n (e.g., 1), of uncorrelated ECG or PPG pulse detections occur within a number, m, of most recent ECG and PPG pulse detections. The number m may be predetermined (e.g., 3) or run-time calculable.

Sub-rule 1a: When the number m is calculable, it is equal to the lesser of the number of either ECG or PPG pulses detected since the last time either the ECG or PPG signal was either noise or lacking as determined by Rules 3 through 6, but never smaller than a first predetermined number, a (e.g., 2), or larger than a second predetermined number, b (e.g., 3).

Rule 2: While the current sensor contact status is good, if more than a predetermined number, y·x (e.g., 1), of uncorrelated EGG or PPG pulse detections occur in a number, y, of the most recent ECG and PPG pulse detections. The number y may be predetermined (e.g., 4) or run-time calculable.

Sub-rule 2a: When the number v is calculable, it is equal to the lessor of the number of either ECG or PPG pulses detected since the last time either the ECG or PPG signal was either noise or lacking as determined by Rules 3 through 6, but never smaller than a first predetermined number, c (e.g., 2), or larger than a second predetermined number, d (e.g., 4).

Rule 3: Rectified ECG signal level greater than a predetermined multiple, r (e.g., 4), of the current ECG detection threshold.

Rule 4: PPG system detects an unstable PPG signal.

Rule 5: No ECG pulses detected for a predetermined period of time (e.g., 3 seconds).

Rule 6: No PPG pulses detected for a predetermined period of time (e.g., 3 seconds).

The following examples illustrate the practical application of the methods described above in the specialized device built to measure ECG and PPG sensor contact failures.

FIG. 17 is a plot depicting poor ECG contact following recent sensor placement. Immediately following sensor contact with the user, the ECG and PPG signals are not yet stable. When the sensors first contact the user, the sensor signals are absent or noisy. In accordance with Rule 1, the sensor quality is considered poor until at least 2 of the last 3 detected ECG and PPG events are correlated. This is indicated by trace 1700 moving to the middle level position after the two correlated events are detected.

FIG. 18 is a plot depicting uncorrelated pulse detection. In accordance with Rule 2, once at least 2 of the last 4 ECG or PPG pulses do not have a correlated PPG or ECG pulse, respectively, the sensor contact application determines a first correlation state failure, and the signal quality is considered to be poor, as indicated by the trace 1800.

Figure 12:
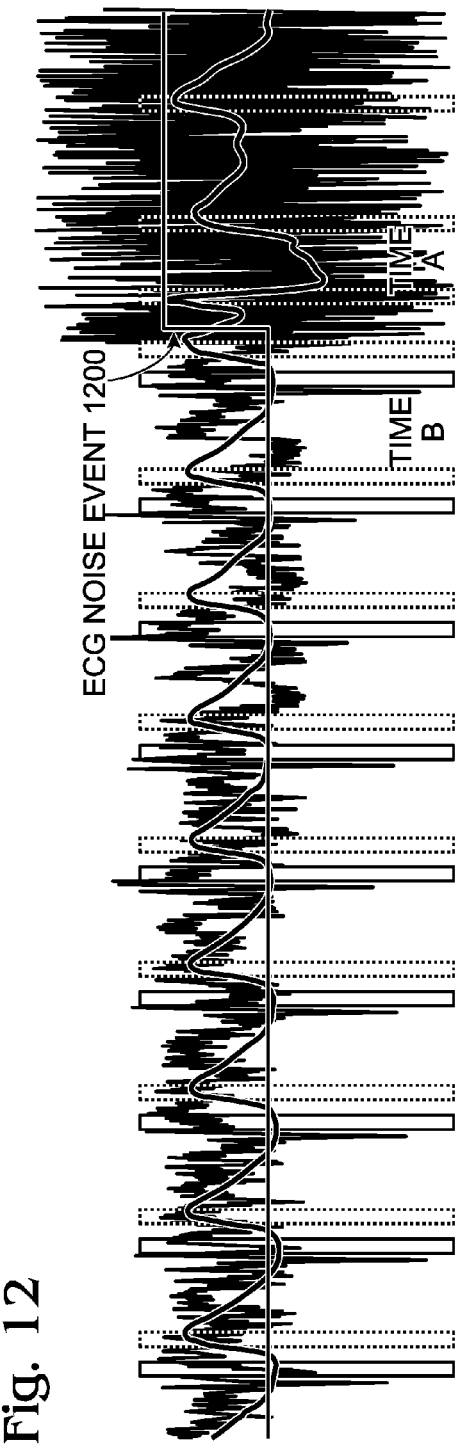
FIG. 12 is a plot depicting the probable loss of contact by an ECG sensor.

FIG. 12 is a plot depicting the probable loss of contact by an ECG sensor. In accordance with Rule 3, the sensor contact application compares a subsequent ECG signal level (e.g., at time A) to an immediately previous detection threshold level (at time B). In response to the subsequent ECG signal level exceeding the immediately previous detection threshold level by a factor of r, where r is a value greater than zero, the sensor contact application determines a second correlation states failure, missing ECG signal, and excludes all previously occurring ECG and PPG signals from subsequent correlation state determinations.

ECG sensor removal can be detected by comparing the threshold level from the ECG detection system with the current filtered and rectified ECG sample. When the ECG sensor is removed, the ECG signal amplitude quickly jumps to a level where the filtered and rectified ECG signal is much larger than the current ECG event detection threshold level. If it is larger than the threshold by a predetermined multiplier (e.g., 4), then the ECG signal quality is considered to be poor. This is indicated by trace 1200 moving up when the electrode is removed from the user.

Figure 13:
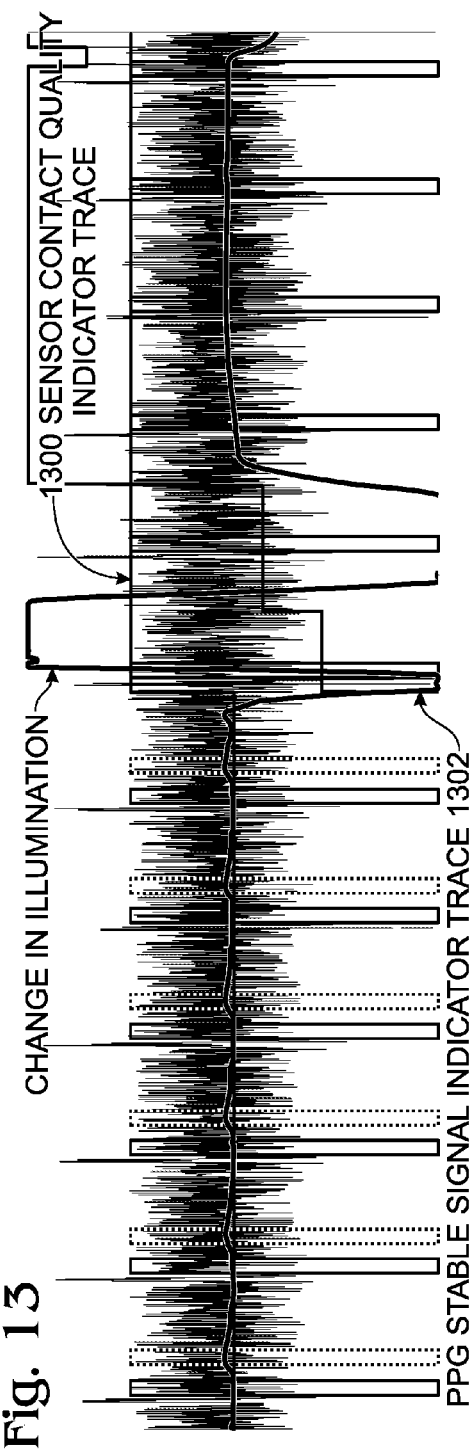
FIG. 13 is a plot depicting the probable loss of contact by a PPG sensor.

FIG. 13 is a plot depicting the probable loss of contact by a PPG sensor. In accordance with Rule 4, the sensor contact application determines a third correlation state failure in response to the light sensing device detecting a change of illumination greater than a within a predetermined time period, where z is a value greater than zero, and excludes all previously occurring ECG and PPG signals from subsequent correlation state determinations.

PPG sensor removal can be detected by the using the stable signal indicator from the PPG detection system. A stable signal is indicated by trace 1302 at the very bottom of the image. The trace moves up from the bottom when the PPG system recognizes that the PPG, sensor is no longer contacting the user, indicating the poor sensor contact. Good sensor contact is indicated by the trace being located at the midpoint of the image. The sensor contact quality indicator trace 1300 moves up to indicate poor sensor contact quickly after the PPG system indicates that the PPG sensor is no longer touching the user.

Figure 14:
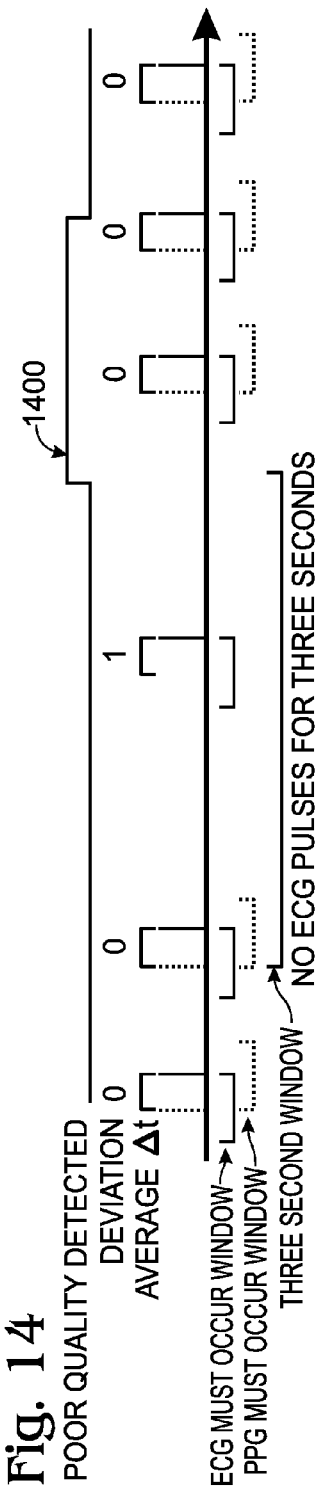
FIG. 14 is a plot depicting the loss of ECG signals.

FIG. 14 is a plot depicting the loss of ECG signals. In accordance with Rule 5, the sensor contact application determines a fourth correlation state failure in response to a failure in measuring ECG signals within a predetermined time period (e.g., 3 seconds), and excludes all previously occurring ECG and PPG signals from subsequent correlation state determinations. This is indicated by trace 1400 moving up when the sensor is removed from the user.

Figure 15:
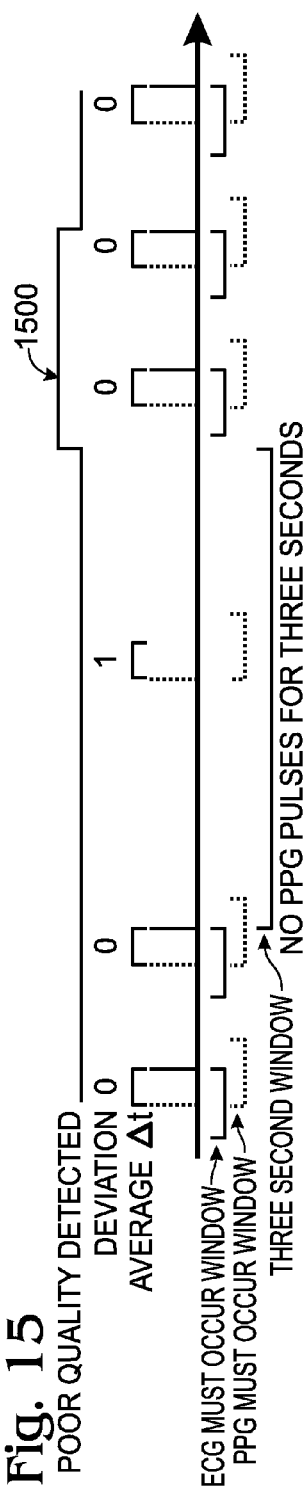
FIG. 15 is a plot depicting the loss of PPG signals.

FIG. 15 is a plot depicting the loss of PPG signals. In accordance with Rule 6, the sensor contact application determines a fifth correlation state failure in response to a failure in measuring PPG signals within a predetermined time period (e.g., 3 seconds), and excludes all previously occurring ECG and PPG signals from subsequent correlation state determinations. This is indicated by trace 1500 moving up when the sensor is removed from the user.

Figure 16:
FIG. 16 is a plot depicting environmental noise causing erroneous ECG signal detection.

FIG. 16 is a plot depicting environmental noise causing erroneous EGG signal detection. Poor sensor contact can be detected by the absence of PPG detection events (Rule 4) or by lack of correlation between ECG and PPG pulses (Rule 2). Since only ECG detection events exist, they are considered to be occurring from poor sensor contact. This is indicated by the sensor contact quality indicator trace 1600 being up from the middle of the image.

In accordance with Sub-rule 1a, any number (greater than or equal to one) of correlated ECG and PPG events from any number (greater than or equal to the number of required correlated events) of recent events can be used to indicate sensor contact quality is good. The greater the number of required correlated events, the greater the probability that the sensor contact is good, but also the longer the amount of time the system requires to make the determination.

In accordance with Sub-rule 2a, any number (greater than or equal to one) of uncorrelated ECG and PPG events from any number (greater than or equal to the number of required uncorrelated events) of recent events can be used to indicate sensor contact quality is poor. The smaller the number of required correlated events, the smaller the amount of time the system requires to make the determination, but also the more sensitive the system is to small amounts of spurious noise.

In addition to the binary good/poor quality metric, a scaled quality metric can also be calculated by taking the ratio of recent correlated events to the total number of recent events. The closer the ratio is to one, the better the sensor contact quality. If no recent events have occurred, then the quality would be set to zero. The number of recent events can be reset to zero when sensor noise or removal is detected as described earlier in this disclosure by using the ECG detection threshold, the PPG stable signal indicators, and the lack of ECG or PPG pulses.

FIGS. 19A and 19B are flowcharts illustrating a method for determining sensor contact in a multi-sensor device. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. When the system powers up, it sets the correlation state to reset state of the ECG and PPG counts equaling zero and their correlation states set to false. The method starts at Step 1900.

Using a first sensor, Step 1902 measures a series of PPG heart beat signals. Using a second sensor. Step 1904 simultaneously measures a series of ECG heart beat signals. Step 1906 detects a correlation in time between each of a plurality of PPG signals and corresponding ECG signals. In response to the timing between correlated PPG and ECG signals remaining within a first correlation deviation limit, Step 1908 determines a correlation state. Since the system powered up with the correlation state reset to false, Rule 1 is described.

The correlation state of Rule 1 is determined in Step 1908 in response to n out of m number of correlated PPG and ECG signals remaining within the correlation deviation limit, where n and m are integers greater than zero. In one aspect, the number of m signals is the larger of two numbers in a first set of numbers, where the first set contains a first predetermined number (a) and a calculated number. The calculated number is the smaller of three numbers in a second set of numbers, where the second set contains a second predetermined number (b), the number of measured ECG signals, and the number of measured PPG signals (Sub-rule 1a).

Subsequent to determining the correlation state, and in response to less than x out of y number of correlated PPG and ECG signals occurring within the correlation deviation limit, where x and y are integers greater than zero, Step 1910 determines a first correlation state failure (Rule 2).

In one aspect, the number of y signals is the larger of two numbers in a first set of numbers, where the first set contains a first predetermined number (c) and a calculated number. The calculated number is the smaller of three numbers in a second set of numbers, where the second set contains a second predetermined number (d), the number of measured ECG signals, and the number of measured PPG signals (Sub-rule 2a).

In one aspect, Step 1912 supplies a signal responsive to the relationship between n and m via a UI, so that the correlation state measurements can be monitored by a subject, patient or caregiver. Measuring the ECG signals in Step 1904 typically includes attaching a pair of ECG sensor electrodes to a corresponding pair of test subject body locations, and the correlation state detected in Step 1908 may include modifying the ratio of n to m in response the body locations selected for the ECG signal measurement.

In another aspect, detecting the correlation in time in Step 1906 includes correlating a leading edge of a first PPG signal to a previous ECG R-wave occurring no more than p milliseconds before the first PPG signal, where p is a value greater than zero. In one scenario, the following substeps are used. Step 1906a determines a plurality of previous ECG signals occurring no more than p milliseconds before the first PPG signal. Step 1906b eliminates from the plurality of previous ECG signals any ECG signals occurring before a prior PPG signal, where the prior PPG signal occurs before the first PPG signal. Step 1906c correlates the first PPG signal to the last occurring ECG signal in the plurality of previous ECG signals. In response to the plurality of previous ECG signals having no members, Step 1906d determines that the correlation deviation limit associated with the first PPG signal has been exceeded.

Alternatively. Step 1906e determines a plurality of subsequent PPG signals occurring no more than p milliseconds subsequent to a first ECG signal. Step 1906f removes from the plurality of PPG signals any PPG signals occurring subsequent to a second ECG signal, where the second ECG signal occurs subsequent to the first ECG signal. In response to the plurality of subsequent PPG signals having no members. Step 1906g determines that the correlation deviation limit associated with the first ECG signal has been exceeded.

In another aspect, measuring the series of EC signals includes in Step 1904 includes comparing a subsequent ECG signal level to an immediately previous detection threshold level. Then, Step 1914 determines a second missing sensor failure in response to the subsequent ECG signal level exceeding the immediately previous detection threshold level by a factor of r, where r is a value greater than zero (Rule 3). Step 1916 excludes all previously occurring ECG and PPG signals from subsequent correlation state determinations.

Measuring PPG signals includes in Step 1902 typically includes the substeps of providing a light emission device (Step 1902a) and providing a light sensing device detecting changes in an optical transmittance of an illuminated test subject body (Step 1902b). In response to the light sensing device detecting a change of illumination greater than z within a predetermined time period, where z is a value greater than zero (Rule 4), Step 1918 determines a third correlation state failure and Step 1916 excludes all previously occurring EC and PPG signals from subsequent correlation state determinations.

In other variations, Step 1905 determines a fourth correlation state failure in response to a failure in measuring ECG signals within a predetermined time period (Rule 5), then Step 1916 excludes all previously occurring ECG and PPG signals from subsequent correlation state determinations. Similarly, Step 1903 determines a fifth correlation state failure in response to a failure in measuring PPG signals within a predetermined time period (Rule 6), then Step 1916 excludes all previously occurring ECG and PPG signals from subsequent correlation state determinations.

Figure 20:
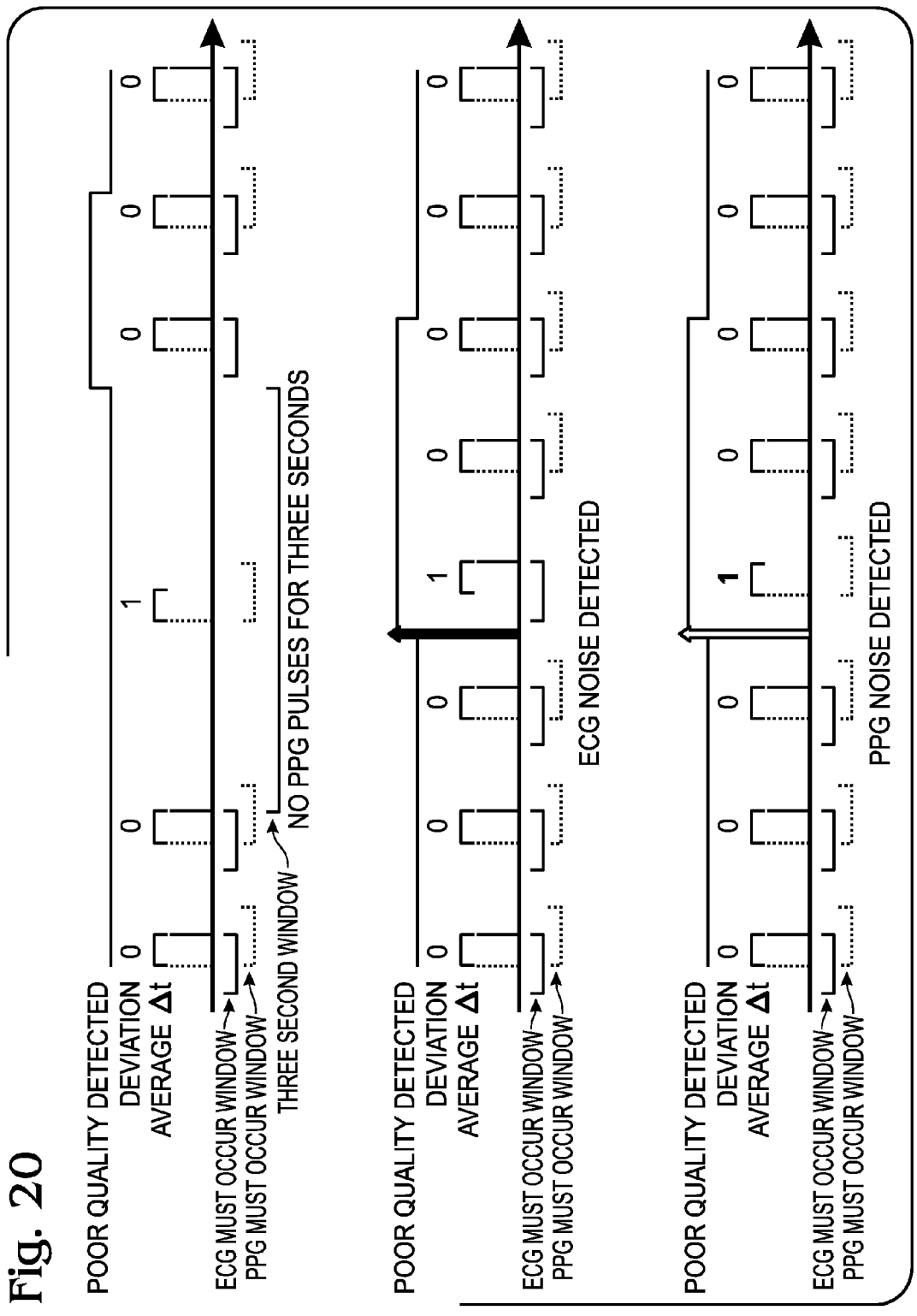
FIGS. 20 and 21, are timing diagrams depicting examples of Rules 1 through 6.
Figure 21:
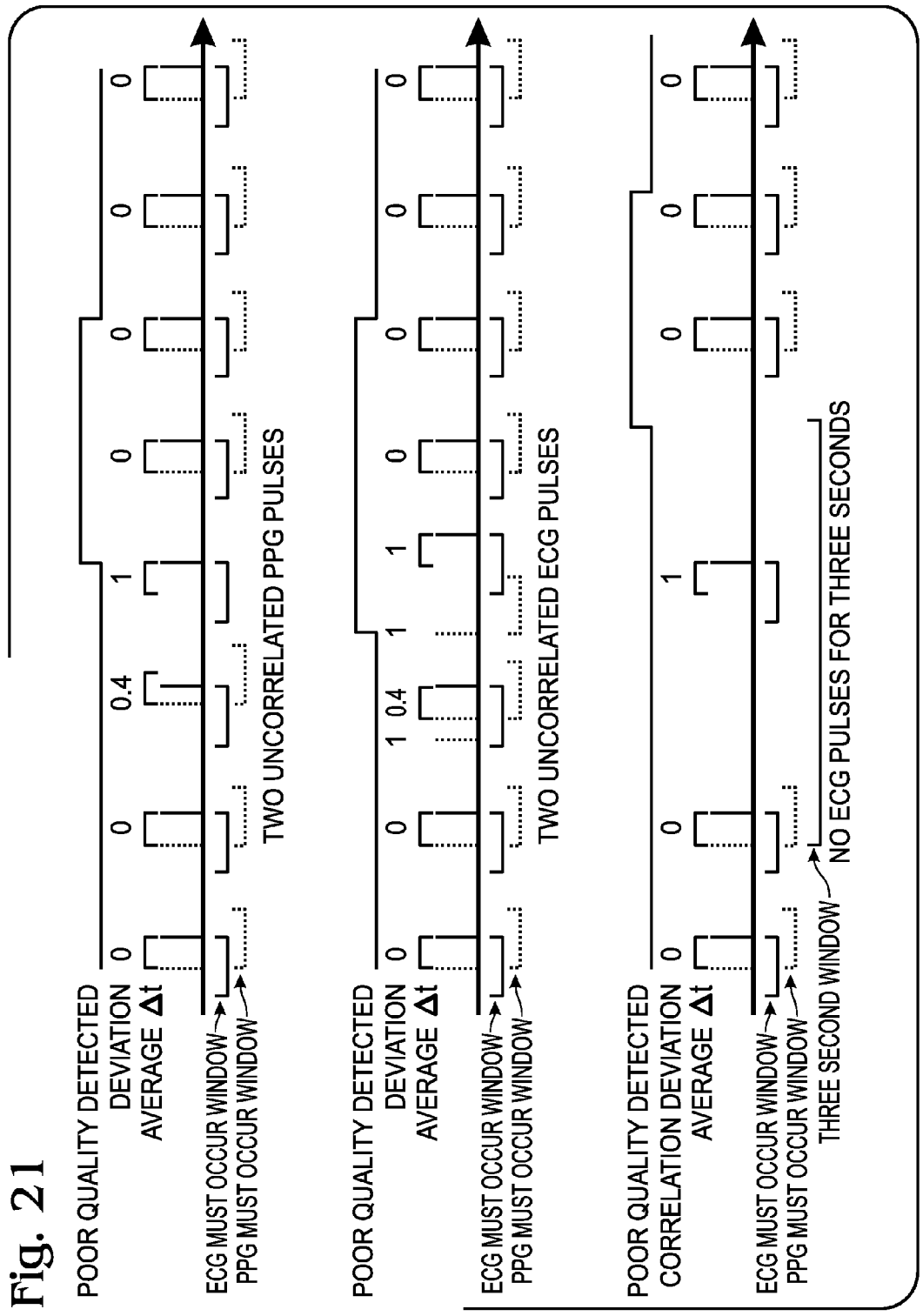

FIGS. 20 and 21 are timing diagrams depicting examples of Rules 1 through 6. In the top diagram of FIG. 20, a Rule 6 violation is depicted when no PPG pulses are detected for 3 seconds. Rule 1 and 1a violations are depicted when there are less than two correlated pulses occurring after a PPG signal is missing. In the center diagram, a violation of Rule 3 is depicted as a result of an increase in ECG signal level. Rules 1 and 1a are also depicted. In the bottom diagram, a violation of Rule 4 is depicted due to a change in PPG signal level. Again, Rules 1 and 1a are depicted.

In the top diagram of FIG. 21, a violation of Rules 2 and 2a is depicted, as more than one uncorrelated PPG pulse is detected during the last four pulses while the sensors are good. Rules 1 and 1a are also violated as more than 1 uncorrelated PPG pulse occurs during the last three pulses when the sensor condition is bad. In the center diagram, a violation of Rules 2 and 2a is depicted, as more than one uncorrelated ECG pulse is detected during the last four pulses while the sensors are good. Rules 1 and 1a are also violated as more than 1 uncorrelated ECG pulse occurs during the last three pulses when the sensor condition is bad.

In the bottom diagram Rule 6 is violated as no ECG pulses occur for three seconds. Again. Rules 1 and 1a are violated.

A system and method have been provided for detecting sensor failures. Examples of particular message structures, processors, and hardware units have been presented to illustrate the invention. However, the invention is not limited to merely these examples. Other variations and embodiments of the invention will occur to those skilled in the art.

I claim:

1. A system for determining sensor contact in a multi-sensor device, the system comprising:
    a first sensor having an output to supply measured photoplethysmography (PPG) signals;
    using a second sensor having an output to supply measured electrocardiogram (ECG) signals;
    a processor;
    a non-transitory memory;
    a sensor contact application residing in the non-transitory memory comprising a sequence of processor instructions, the sensor contact application receiving the PPG and ECG signals, detecting a correlation in time between PPG signals and corresponding ECG signals, and in response to the timing between correlated PPG and ECG signals remaining within a correlation deviation limit, determining a correlation state;
    wherein the sensor contact application determines the correlation state has occurred when n out of m number of correlated PPG and ECG signals occur within the correlation deviation limit, where n and m are integers greater than zero; and,
    wherein the correlation state indicates a satisfactory quality of sensor contact with a user.

2. The system of claim 1 wherein the number of m signals is the larger of two numbers in a first set of numbers, where the first set contains a first predetermined number and a calculated number; and where the calculated number is the smaller of three numbers in a second set of numbers, where the second set contains a second predetermined number, the number of measured ECG signals, and the number of measured PPG signals.

3. The system of claim 1 further comprising:
    a user interface (UI) having an input connected to the sensor contact application for accepting a signal responsive to the relationship between n and m, and an output to present the relationship between n and m.

4. The system of claim 3 wherein the second sensor comprises a pair of ECG sensor electrodes attachable to a corresponding pair of test subject body locations;
    wherein the UI has an input for accepting information concerning test subject body locations and an output for supplying the information to the sensor contact application; and,
    wherein the sensor contact application determines the correlation state by modifying the ratio of n to m in response the body locations selected for the ECG signal measurement.

5. The system of claim 1 wherein the sensor contact application detects the correlation in time by correlating a leading edge of a first PPG signal to a previous ECG R-wave occurring no more than p milliseconds before the first PPG signal, where p is a value greater than zero.

6. The system of claim 5 wherein the sensor contact application detects the correlation in time as follows:
    measuring a plurality of previous ECG signals occurring no more than p milliseconds before the first PPG signal;
    eliminating from the plurality of previous ECG signals any ECG signals occurring before a prior PPG signal, where the prior PPG signal occurs before the first PPG signal; and,
    correlating the first PPG signal to the last occurring ECG signal in the plurality of previous ECG signals.

7. The system of claim 6 wherein the sensor contact application detects the correlation in time by determining that the correlation deviation limit associated with the first PPG signal has been exceeded in response to the plurality of previous ECG signals having no members.

8. The system of claim 1 wherein the sensor contact application detects the correlation in time as follows:
    measuring a plurality of subsequent PPG signals occurring no more than p milliseconds subsequent to a first ECG signal;
    removing from the plurality of PPG signals any PPG signals occurring subsequent to a second ECG signal, where the second ECG signal occurs subsequent to the first ECG signal; and,
    in response to the plurality of subsequent PPG signals having no members, determining that the correlation deviation limit associated with the first ECG signal has been exceeded.

9. The system of claim 1 wherein the sensor contact application, after initially determining the correlation state, determines a first correlation state failure in response to less than x out of y number of correlated PPG and ECG signals occurring within the correlation deviation limit, where x and y are integers greater than zero.

10. The system of claim 9 wherein the number of y signals is the larger of two numbers in a first set of numbers, where the first set contains a first predetermined number and a calculated number, and where the calculated number is the smaller of three numbers in a second set of numbers, where the second set contains a second predetermined number, the number of measured ECG signals, and the number of measured PPG signals.

11. The system of claim 1 wherein the sensor contact application compares a subsequent ECG signal level to an immediately previous detection threshold level, and in response to the subsequent ECG signal level exceeding the immediately previous detection threshold level by a factor of r, where r is a value greater than zero, determines a second missing sensor failure, and excludes all previously occurring ECG and PPG signals from subsequent correlation state determinations.

12. The system of claim 1 wherein the first sensor comprises:
    a light emission device;
    a light sensing device detecting changes in an optical transmittance of an illuminated test subject body; and,
    wherein the sensor contact application determines a third correlation state failure in response to the light sensing device detecting a change of illumination greater than z within a predetermined time period, where z is a value greater than zero, and excludes all previously occurring ECG and PPG signals from subsequent correlation state determinations.

13. The system of claim 1 wherein the sensor contact application determines a fourth correlation state failure in response to a failure in measuring ECG signals within a predetermined time period, and excludes all previously occurring ECG and PPG signals from subsequent correlation state determinations.

14. The system of claim 1 wherein the sensor contact application determines a fifth correlation state failure in response to a failure in measuring PPG signals within a predetermined time period, and excludes all previously occurring ECG and PPG signals from subsequent correlation state determinations.

15. A system for determining sensor contact in a multi-sensor device, the system comprising:
a first sensor having an output to supply measured photoplethysmography (PPG) signals;
using a second sensor having an output to supply measured electrocardiogram (ECG) signals;
a processor;
a non-transitory memory;
a sensor contact application residing in the non-transitory memory comprising a sequence of processor instructions, the sensor contact application receiving the PPG and ECG signals, detecting a correlation in time between PPG signals and corresponding ECG signals, and in response to the timing between correlated PPG and ECG signals remaining within a correlation deviation limit, determining a correlation state;
wherein the sensor contact application detects the correlation in time as follows:
measuring a plurality of subsequent PPG signals occurring no more than p milliseconds subsequent to a first ECG signal;
removing from the plurality of PPG signals any PPG signals occurring subsequent to a second ECG signal, where the second ECG signal occurs subsequent to the first ECG signal;
in response to the plurality of subsequent PPG signals having no members, determining that the correlation deviation limit associated with the first ECG signal has been exceeded; and,
wherein the correlation state indicates a satisfactory quality of sensor contact with a user.

16. The system of claim 15 wherein the number of m signals is the larger of two numbers in a first set of numbers, where the first set contains a first predetermined number and a calculated number; and where the calculated number is the smaller of three numbers in a second set of numbers, where the second set contains a second predetermined number, the number of measured ECG signals, and the number of measured PPG signals.

17. The system of claim 15 wherein the sensor contact application detects the correlation in time by correlating a leading edge of a first PPG signal to a previous ECG R-wave occurring no more than p milliseconds before the first PPG signal, where p is a value greater than zero.

18. A system for determining sensor contact in a multi-sensor device, the system comprising:
a first sensor having an output to supply measured photoplethysmography (PPG) signals;
using a second sensor having an output to supply measured electrocardiogram (ECG) signals;
a processor;
a non-transitory memory;
a sensor contact application residing in the non-transitory memory comprising a sequence of processor instructions, the sensor contact application receiving the PPG and ECG signals, detecting a correlation in time between PPG signals and corresponding ECG signals, and in response to the timing between correlated PPG and ECG signals remaining within a correlation deviation limit, determining a correlation state;
wherein the sensor contact application compares a subsequent ECG signal level to an immediately previous detection threshold level, and in response to the subsequent ECG signal level exceeding the immediately previous detection threshold level by a factor of r, where r is a value greater than zero, determines a second missing sensor failure, and excludes all previously occurring ECG and PPG signals from subsequent correlation state determinations; and,
wherein correlation state indicates a satisfactory quality of sensor contact with a user.

19. The system of claim 18 wherein the number of m signals is the larger of two numbers in a first set of numbers, where the first set contains a first predetermined number and a calculated number; and where the calculated number is the smaller of three numbers in a second set of numbers, where the second set contains a second predetermined number, the number of measured ECG signals, and the number of measured PPG signals.

20. The system of claim 18 wherein the sensor contact application detects the correlation in time by correlating a leading edge of a first PPG signal to a previous ECG R-wave occurring no more than p milliseconds before the first PPG signal, where p is a value greater than zero.

* * * * *